United States Patent
Ohno et al.

(10) Patent No.: US 6,277,993 B1
(45) Date of Patent: Aug. 21, 2001

(54) INTERMEDIATES FOR 5-SUBSTITUTED-3-OXADIAZOLYL-1,6-NAPHTHYRIDIN-2(1H)-ONE DERIVATIVES

(75) Inventors: Kazunori Ohno, Ikoma; Osamu Odai, Hirakata; Kaoru Masumoto, Neyagawa; Kiyoshi Furukawa, Shiga-ken; Makoto Oka, Ibaraki, all of (JP)

(73) Assignee: Dainippon Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/654,782

(22) Filed: Sep. 1, 2000

Related U.S. Application Data

(62) Division of application No. 09/462,412, filed as application No. PCT/JP98/03134 on Jul. 19, 1998, now Pat. No. 6,172,079.

(30) Foreign Application Priority Data

Jul. 15, 1997  (JP) .................................................. 9-207179

(51) Int. Cl.$^7$ .................................................. C07D 471/04
(52) U.S. Cl. .......................................... 546/122; 546/123
(58) Field of Search ...................................... 546/122, 123

(56) References Cited

U.S. PATENT DOCUMENTS

| | | | |
|---|---|---|---|
| 4,415,580 | 11/1983 | Lesher et al. | 424/263 |
| 5,294,620 | * 3/1994 | Ratcliffe et al. | 546/122 |

FOREIGN PATENT DOCUMENTS 0 588 500   3/1994 (EP) .

OTHER PUBLICATIONS

Grant et al, Grant and Hack's Chem. Dictionary, McGraw Hill, P. 112, 1987.*
W. Tully et al., "2–(Oxadiazolyl)–and 2–(Thiazolyl)imidazo[1,2–α]pyrimidines as Agonists and Inverse Agonists at Benzodiazepine Receptors", Journal of Medicinal Chemistry, vol. 34, pp. 2060–2067, 1991.
C. Braestrup et al., "Benzodiazepine Receptor Ligands with Positive and Negative Efficacy", Neuropharmacology, vol. 22, No. 12B, pp. 1451–1457, 1983.
C. Gardner, "Interpretation of the Behavioral Effects of Benzodiazepine Receptor Ligands", Drugs of the Future, vol. 14, No. 1, pp. 51–67, 1989.
P. Molina et al., "Iminophosphorane–Mediated Synthesis of 3,5–Disubstituted 1,2,4–Oxadiazoles", Synthesis, pp. 843–845, 1986.
L. Whitfield et al., "Heterocycles from N–Benzoylthioamides and Dinucleophilic Reagnets", Journal of Heterocyclic Chemistry, vol. 18, pp. 1197–1201, 1981.
Kou–Chang Liu et al., "A Particularly Convenient Preparation of Benzohydroximinoyl Chlorides (Nitrile Oxide Precursors)", Journal of Organic Chemistry, vol. 45, pp. 3916–3918, 1980.
Synthesis, pp. 102–103, 1979 (not in English).
B. Singh et al., "A Facile and Novel Synthesis of 1,6–Naphthyridin–2(1H)–ones", Journal of Heterocyclic Chemistry, vol. 27, pp. 2085–2091, 1990.
B. Singh et al., "Novel cAMP PDE III Inhibitors: 1,6–Naphthyridin–2–(1H)–ones", Journal of Medicinal Chemistry, vol. 35, pp. 4858–4865, 1992.
H. Fukatsu et al., "Synthesis and Cardiotonic Activity of 5–(2–Substituted Thiazol–4–YL)–2–Pyridones and Thiazolo[4,5–f]Quinolinones", Heterocycles, vol. 29, No. 8, pp. 1517–1528, 1989.
W. Jones et al., "A Convenient Synthesis of 5–Acyl–6–substituted 3–Cyano–2(1H)–pyridinones", Journal of Heterocyclic Chemistry, vol. 27, pp. 511–518 1990.
H. Mohler et al., "Properties of $^3$H–Diazepam Binding to Benzodiazepine Receptors in Rat Cerebral Cortex", Life Sciences, vol. 20, pp. 2101–2110, 1977.
G. Biggio et al., "Enhancement of GABAergic Transmission by zolpidem, an imidazopyridine with preferential affinity for type I benzodiazephine receptors", European Journal of Pharmacology, vol. 161, pp. 173–180, 1989.
A. Matsushita et al., "Activation of Brain Function by S–135, A Benzodiazepine Receptor Inverse Agonist", Progress in Neuro–Psychopharmcology and Biological Psychiatry, vol. 12, pp. 951–966, 1988.
Journal of Medicinal Chemistry, 1990, vol. 35, No. 26, pp. 4858–4865.

* cited by examiner

Primary Examiner—Bernard Dentz
(74) Attorney, Agent, or Firm—Wenderoth, Lind & Ponack, L.L.P.

(57) ABSTRACT

A 5-substituted-3-oxadiazolyl-1,6-naphthyridin-2(1H)-one derivative of the formula (I):

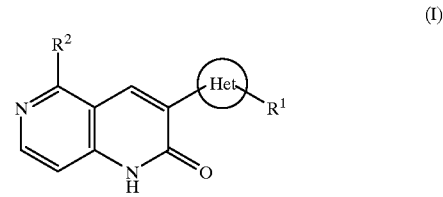

(I)

wherein Het is oxadiazolyl, $R^1$ is H, lower alkyl, cyclo-lower alkyl, trifluoromethyl, lower alkenyl, lower alkynyl, lower alkoxy, lower alkoxy-lower alkyl, hydroxy-lower alkyl, substituted or unsubstituted aryl, or substituted or unsubstituted heteroaromatic group, and $R^2$ is H, lower alkyl, cyclo-lower alkyl, cyclo-lower alkylmethyl, lower alkenyl, cyclo-lower alkenyl, lower alkynyl, substituted or unsubstituted aryl, or substituted or unsubstituted heteroaromatic group, or a pharmaceutically acceptable acid addition salt thereof, which has high selective affinity to benzodiazepine receptor and is useful particularly as a benzodiazepine inverse agonist, for example, as psychoanaleptic drug or a drug for the treatment of dysmnesia in senile dementia or Alzheimer's disease.

1 Claim, No Drawings

INTERMEDIATES FOR 5-SUBSTITUTED-3-OXADIAZOLYL-1,6-NAPHTHYRIDIN-2(1H)-ONE DERIVATIVES

This is a divisional application of Ser. No. 09/462,412 filed Jan. 10, 2000 now U.S. Pat. No. 6,172,079, which is a 371 of PCT/JP98/03134 filed Jul. 14, 1998.

TECHNICAL FIELD

The present invention relates to novel a 5-substituted-3-oxadiazolyl-1,6-naphthyridin-2(1H)-one derivative or a pharmaceutically acceptable acid addition salt thereof which is useful as a medicament, and use thereof as a medicament, and further intermediates for preparing the same.

BACKGROUND ART

Benzodiazepine (BZP) compounds, such as diazepam which is a representative compound, have anxiolytic activity and hence have been developed as anxiolytic drugs, but they have also anticonvulsant, sedative and hypnotic activities and hence these compounds have been used in wide clinical fields such as (1) anxiolytic drug, (2) sedative (hypnotic) drug, (3) muscular relaxant, and (4) antiepileptic drug.

BZP compounds have mainly the pharmacological activities such as (1) acclimating activity, (2) hypnotic activity, (3) central muscle relaxant activity, (4) anti-convulsant activity. It is understood that these activities are not exhibited by independent mechanism separately, but are induced by closely related neuropharmacological mechanisms.

Since late 1970s, with progress of pharmacological investigation of BZP compounds, there have been found two footings for clarifying the mechanism of exhibiting the activities thereof, one being a phenomenon of increasing γ-aminobutyric acid agonistic (GABAergic) neurotransmittant mechanism of the central nervous system by the BZP drugs, and another being new finding of BZP specific binding site (BZP receptor) and proving of a mechanism of the functional connection between the brain BZP receptor and GABA receptor. As the result of such investigation, it has almost been established that the GABAergic neurotransmittant mechanism participates in the pharmacological activities of BZP compounds.

Administration of BZP compounds induces side effects such as ataxia, hypnosis, muscle relaxation or lowering of ability of cognition or reflex movement and further formation of resistance and dependence to the drugs, and hence, there are many problems to be improved in the BZP compounds. Studies have been made on non-BZP compounds which have a different chemical structure from BZP compounds but have similar functions in the activation mechanisms. Those compounds including such non-BZP compounds are called as benzodiazepine receptor agonistic drugs. As the non-BZP compounds, there are known, for example, the compounds having the chemical formulae (A), (B) and (C) as shown below.

The compounds having the formulae (A) and (B) are disclosed in Journal of Medicinal Chemistry, vol. 34, p. 2060 (1991).

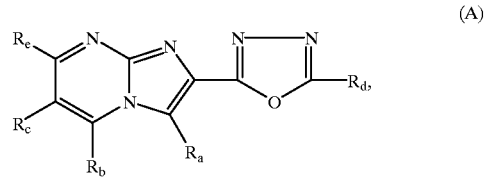

(A)

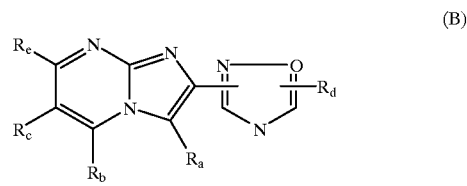

(B)

wherein $R_a$ is a hydrogen atom, $R_b$–$R_d$ are a methyl group, etc., and $R_e$ is a methoxy group, etc.

The compounds of the formula (C) are disclosed in EP-A2-0588500.

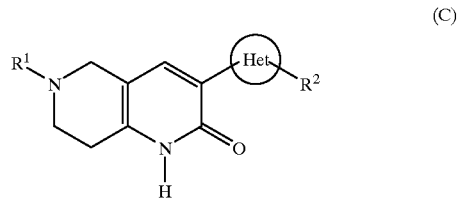

(C)

wherein Het is an oxadiazolyl group, $R^1$ is a benzyl group, etc. and $R^2$ is a methoxy group, etc.

However, with progress of investigation, there has been found a certain compound among the non-BZP compounds, which has similar high selective affinity to the benzodiazepine (BZP) receptor but has entirely inverse activities [Braestrup, C. et al., Neuropharmacol., 22, pp.1451–1457 (1983)]. When these compounds are administered, they exhibit pharmacological activities such as convulsion increasing activity, anxiety inducing activity, muscle hypertonia. Accordingly, the old BZP compounds which have hitherto been used as anxiolytic drugs are defined as an agonist, and the compounds having thus inverse activities are defined as an inverse agonist.

Since these inverse agonists have been found, intensive studies have been done on the correlation between the modifying (binding) manner and the pharmacological activities of the compounds which bind (exhibit affinity) to the BZP receptor. According to these studies, it has been found that the BZP receptor is present between the GABA receptor (an depressive neurotransmittant) and a chloride ion channel and is a molecular unit to form a complex. The GABA receptor includes an ion channel type $GABA_A$ receptor and a metabolism controlling type $GABA_B$ receptor, and the $GABA_A$ receptor forms a complex with a BZP receptor and the Cl ion channel. The compounds to be bound to the BZP receptor are now classified into an agonist (further subsequently classified into a full agonist and a partial agonist), an inverse agonist (further subsequently classified into a full inverse agonist and a partial inverse agonist) and an antagonist.

The agonist binds selectively to the BZP compounds and thereby acts increasing coupling of the GABA receptor and the Cl ion channel and increases flowing of Cl ion into cells owing to increase of open-close frequency of the Cl ion channel and then stimulates the cell activities owing to decrease of negative electric charge (increases cell stimulation). It is said that the antagonist does not change the coupling function thereof but inhibits binding of the agonist or inverse agonist to the BZP receptor.

There are many method for checking the manner of binding of the compounds to the benzodiazepine receptor, and one of the known methods is a TBPS binding assay. As mentioned here in before, the $GABA_A$ receptor forms a complex with a BZP compound receptor and the Cl ion channel, and it is known that a neurosteroid receptor is present on the $GABA_A$ receptor membrane and a TBPS(t-butylbicyclophosphonothionate) bond recognizing site is located around the Cl ion channel. The function of GABA to the nervous system is modified and controlled by controlling of the opening of the Cl ion channel and transmission of Cl ion into cells within the $GABA_A$ receptor complex molecule under complicated mutual effects. By checking many drugs which act directly or indirectly on the function of the $GABA_A$ receptor complex, it is known that there is a good inverse correlation between the test data of TBSP binding and the test data of Cl ion uptake into cells. For instance, the uptake of Cl ion into cells is decreased by $GABA_A$ receptor agonists (e.g. Muscimol), neurosteroid receptor agonists, diazepam which is the representative benzodiazepaine receptor agonist, or chlonazepam which is a partial agonist, and is increased by benzodiazepine receptor inverse agonist [e.g. DMCM (methyl-6,7-dimethoxy-4-ethyl-β-carboline-3-carboxylate)] and a partial inverse agonist [e.g. FG7142 (N-methyl-β-carboline-3-carboxamide)]. Accordingly, the TBPS binding assay is useful for clarifying the $GABA_A$ receptor function, the in vitro biochemical screening of the drugs acting via allosteric binding site of bezodiazepine drugs, $GABA_A$ receptor complex, etc., and the acting mechanisms of the drugs.

Most of the old BZP compounds such as the compounds of the formulae (A), (B) and (C) have agonistic properties. On the contrary, some compounds having inverse agonistic properties are known, for example, the compounds of the following formulae (D) and (E) (DMCM and FG7142):

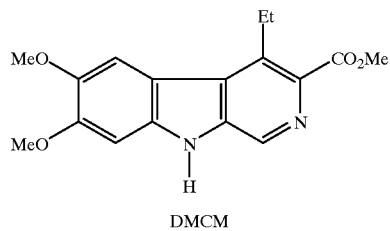

DMCM

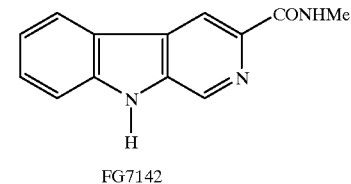

FG7142

The DMCM and FG7142 are disclosed in Colin R. Gardner, Drugs of the Future, vol. 14, pp. 51–67 (1987).

In addition, many investigations have also been made on the correlation between the binding manner to the benzodiazepine receptor and the pharmacological activities of the compounds. As mentioned above, the BZP agonists have been used as anxiolytic drug, hypnotic disorder curing agent (sleep inducing drug) or antiepileptic drug, but it is known that in addition to these activities, they have also an amnestic activity in animals including also human being. Accordingly, BZP inverse agonists are expected to have activities inverse to the amnesia inducing activity, that is, anti-amnestic activity, psychoanaleptic activity. Moreover, it is known that the activity of acetylcholine, which has an important relation to cognition function, is decreased by the BZP agonists and is increased by the BZP inverse agonists, and hence the BZP inverse agonists are expected to exhibit cognition enhancing activity. Thus, it has been expected that the BZP inverse agonists may be useful as psychoanaleptic drug and a drug for treating dysmnesia in senile dementia, cerebrovascular and Alzheimer's dementia.

There is no report as to the compounds of the present invention which have the formula (I) described hereinafter and have high selective affinity to a benzodiazepine receptor and particularly acts as a BZP inverse agonist.

DISCLOSURE OF THE INVENTION

This invention provides a novel 5-substituted-3-oxadiazolyl-1,6-naphthyridin-2(1H)-one derivative having the following formula (I) or a pharmaceutically acceptable acid addition salt thereof which has high selective affinity to a benzodiazepine receptor, and a use thereof as a medicament.

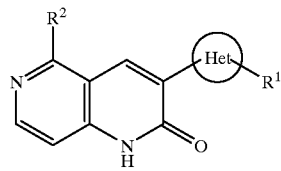

(I)

wherein Het is an oxadiazolyl group, $R^1$ is a hydrogen atom, a lower alkyl group, a cyclo-lower alkyl group, a trifluoromethyl group, a lower alkenyl group, a lower alkynyl group, a lower alkoxy group, a lower alkoxy-lower alkyl group, a hydroxy-lower alkyl group, a substituted or unsubstituted aryl group, or a substituted or unsubstituted heteroaromatic group, and $R^2$ is a hydrogen atom, a lower alkyl group, a cyclo-lower alkyl group, a cyclo-lower alkylmethyl group, a lower alkenyl group, a cyclo-lower alkenyl group, a lower alkynyl group, a substituted or unsubstituted aryl group, or a substituted or unsubstituted heteroaromatic group.

This invention further provides novel 1,6-naphthyridin-2(1H)-one derivatives of the following formula (I') which are useful as an intermediate for preparing 5-substituted-3-oxadiazolyl-1,6-naphthyridin-2(1H)-one derivatives of the above formula (I) useful as a medicament.

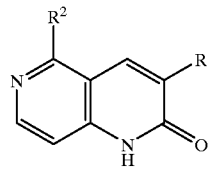

(I')

wherein R is a cyano group, a carbamoyl group, a carboxyl group, a lower alkoxycarbonyl group, or a substituted or unsubstituted benzyloxycarbonyl group, and $R^2$ is a lower alkyl group, a cyclo-lower alkyl group, a lower alkenyl group, a cyclo-lower alkenyl group, a lower alkynyl group, a substituted or unsubstituted aryl group, or a substituted or unsubstituted heteroaromatic group, provided that $R^2$ is not a methyl group or a pyridyl group.

During the intensive studies of non-benzodiazepine compounds having affinity to an intracerebral benzodiazepine receptor, the present inventors have found that the 5-substituted-3-oxadiazolyl-1,6-naphthyridin-2(1H)-one derivatives of the above formula (I) have a high selective affinity to a benzodiazepine (BZP) receptor and hence are useful as a benzodiazepine receptor agonistic drug and further that those compounds include a compound having a BZP agonistic activity and a compound having a BZP inverse agonistic activity which depend on the kinds of combination of the substituents $R^1$ and $R^2$.

Among the compounds of this invention, preferred compounds are the compounds of the formula (I) wherein $R^1$ is a $C_1$–$C_3$ alkyl group, a $C_3$–$C_4$ cycloalkyl group, or a $C_2$–$C_3$ alkenyl group, and $R^2$ is a hydrogen atom, a $C_1$–$C_4$ alkyl group, a $C_3$–$C_6$ cycloalkyl group, a substituted or unsubstituted aryl group, or a substituted or unsubstituted heteroaromatic group.

More preferred compounds are the compounds of the formula (I) wherein $R^1$ is a $C_1$–$C_3$ alkyl group or a $C_3$–$C_4$ cycloalkyl group, and $R^2$ is a hydrogen atom, a $C_1$–$C_3$ alkyl group, a $C_3$–$C_4$ cycloalkyl group, a substituted or unsubstituted phenyl group, or a substituted or unsubstituted heteroaromatic group.

Further preferred compounds are the following compounds. 3-(5-Ethyl-1,2,4-oxadiazol-3-yl)-5-(2-methylcyclopropyl)-1,6-naphthyridin-2(1H)-one, 3-(5-Methyl-1,2,4-oxadiazol-3-yl)-5-(2-methylphenyl)-1,6-naphthyridin-2(1H)-one, 3-(5-Methyl-1,2,4-oxadiazol-3-yl)-5-(3-methoxyphenyl)-1,6-naphthyridin-2(1H)-one, 3-(5-Methyl-1,2,4-oxadiazol-3-yl)-5-(4-methoxyphenyl)-1,6-naphthyridin-2(1H)-one, 3-(5-Ethyl-1,2,4-oxadiazol-3-yl)-5-(2-thienyl)-1,6-naphthyridin-2(1H)-one, 3-(5-Methyl-1,2,4-oxadiazol-3-yl)-5-(4-pyridyl)-1,6-naphthyridin-2(1H)-one, 3-(3-Ethyl-1,2,4-oxadiazol-5-yl)-5-methyl-1,6-naphthyridin-2(1H)-one, 3-(3-Ethyl-1,2,4-oxadiazol-5-yl)-5-(3-fluorophenyl)-1, 6-naphthyridin-2(1H)-one, 3-(3-Methyl-1,2,4-oxadiazol-5-yl)-5-(3-methylphenyl)-1,6-naphthyridin-2(1H)-one, 3-(3-Methyl-1,2,4-oxadiazol-5-yl)-5-(3-methoxyphenyl)-1,6-naphthyridin-2(1H)-one, 3-(3-Ethyl-1,2,4-oxadiazol-5-yl)-5-(4-methoxyphenyl)-1,6-naphthyridin-2(1H)-one, 3-(3-Ethyl-1,2,4-oxadiazol-5-yl)-5-(4-pyridyl)-1,6-naphthyridin-2(1H)-one, and 3-(3-Cyclopropyl-1,2,4-oxadiazol-5-yl)-5-(3-thienyl)-1,6-naphthyridin-2(1H)-one.

The pharmaceutically acceptable acid addition salt of the compounds of the formula (I) includes inorganic acid addition salts such as hydrochloride, hydrobromide, hydroiodide, sulfate, phosphate, and organic acid addition salts such as oxalate, maleate, fumarate, malonate, lactate, malate, citrate, tartrate, benzoate, methanesulfonate, or tosylate.

In the specification, the terms "lower alkyl group" and the "lower alkyl" moiety mean a straight chain or branched chain alkyl group having 1 to 6 carbon atoms, for example, methyl, ethyl, propyl, isopropyl, butyl, isobutyl, tert-butyl, pentyl, and hexyl groups.

The term "cyclo-lower alkyl group" means a cycloalkyl group having 3 to 6 carbon atoms, for example, cyclopropyl, cyclobutyl, cyclopentyl, and cyclohexyl groups, where the ring may be substituted by a $C_1$–$C_3$ alkyl group or a halogen atom.

The terms "lower alkenyl group" and the "lower alkynyl group" have a straight or branched chain having 2 to 6 carbon atoms, and include, for example, allyl, 1-propenyl, propargyl, and 2-methyl-1-ethynyl groups.

The term "cyclo-lower alkenyl group" means a cycloalkyl group having 5 to 6 carbon atoms, for example, cyclohexenyl group.

The terms "lower alkoxy group" and the "lower alkoxy" moiety mean a straight chain or branched chain alkoxy group having 1 to 6 carbon atoms, and include, for example, methoxy, ethoxy, propoxy, isopropyloxy, butyloxy, isobutyloxy, tert-butyloxy, pentyloxy, and hexyloxy groups.

The terms "aryl group" and "aryl" moiety mean a phenyl group or a naphthyl group and the ring thereof may optionally have a 1 to 3 substituents selected from a halogen atom, a $C_1$–$C_3$ alkyl group, a trifluoromethyl group, a hydroxy group, a $C_1$–$C_3$ alkoxy group, a trifluoromethoxy group, a cyano group and an amino group, and a nitro group.

The term "heteroaromatic group" means a 5- or 6-membered aromatic heterocyclic group containing, the same or deifferent, 1 to 2 hetero atoms selected from nitrogen atom, oxygen atom, and sulfur atom, and includes, for example, furyl, thienyl, pyrrolyl, oxazolyl, isoxazolyl, pyridyl, pyridazinyl, and pyrimidinyl, which these heteroaromatic groups may optionally have 1 to 3 substituents selected from a halogen atom, a $C_1$–$C_3$ alkyl group, a hydroxy group, a $C_1$–$C_3$ alkoxy group, and an amino group.

In the "substituted or unsubstituted benzyloxycarbonyl group", the substituent is selected from a $C_1$–$C_3$ alkyl group, a $C_1$–$C_3$ alkoxy group, a cyano group and a nitro group.

The term "halogen atom" means fluorine, chlorine, bromine or iodine atom.

The compounds of this invention may be prepared by the processes 1 to 4 as mentioned below.

Process 1

In the compound of the formula (Ia):

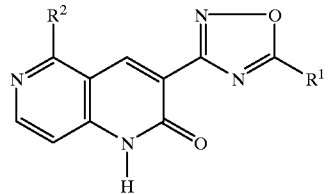

(Ia)

wherein $R^1$ and $R^2$ are the same as defined above, or of the formula (Ib):

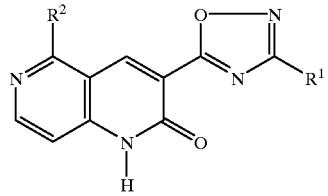

(Ib)

wherein $R^1$ and $R^2$ are the same as defined above, when $R^1$ is a group other than a lower alkoxy group, the compound can be prepared by subjecting a compound of the formula (II):

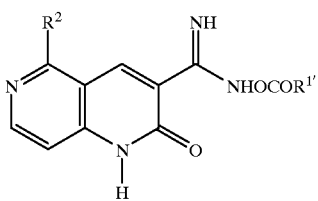

(II)

wherein $R^{1'}$ is the same as $R^1$ other than lower alkoxy group, and $R^2$ is as defined above, or of the formula (III):

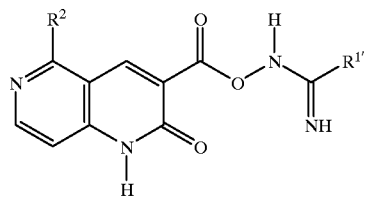

(III)

wherein $R^{1'}$ the same as $R^1$ other than lower alkoxy group, and $R^2$ is as defined above, to an intramolecular cyclization reaction.

The cyclization reaction may be carried out in the presence of a dehydrating agent, but may usually be carried out by heating the compound in an appropriate solvent which does not affect the reaction. The solvent includes aromatic hydrocarbons (e.g. benzene, toluene, xylene), ethers (e.g. tetrahydrofuran, dioxane), N,N-dimethylformamide. These solvents may be used alone or in combination of two or more thereof. The reaction temperature may vary depending on the kinds of the starting materials, etc. but is usually in the range of 50 to 150° C., preferably 80 to 120° C.

Process 2

In the compound of the formula (Ia), when $R^1$ is a lower alkoxy group, the compounds can be prepared by subjecting a compound of the formula (IV):

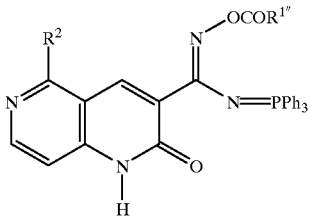

(IV)

wherein $R^{1''}$ is a lower alkoxy group, Ph means a phenyl group, and $R^2$ is the same as defined above, to an intramolecular cyclization reaction in a similar manner as described, for example, in Synthesis, p.843 (1986).

The cyclization reaction is usually carried out by heating the starting compound in an appropriate solvent. The solvent includes aromatic hydrocarbons (e.g. benzene, toluene, xylene), ethers (e.g. tetrahydrofuran, dioxane). The reaction temperature may vary depending on the kinds of the starting materials, etc. but is usually in the range of 50 to 150° C., preferably 80 to 120° C.

Process 3

In the compound of the formula (Ib), when $R^1$ is a lower alkoxy group, the compound can be prepared by reacting a compound of the formula (V):

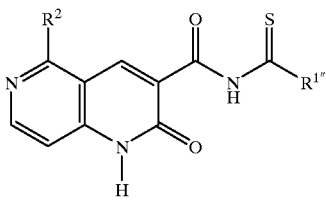

(V)

wherein $R^{1''}$ is a lower alkoxy group, and $R^2$ is the same as defined above, with a hydroxylamine in a similar manner as described, for example, in Journal of Heterocyclic Chemistry, vol. 18, p.1197 (1981).

The reaction is usually carried out in an appropriate solvent. The solvent includes alcohols (e.g. methanol, ehtanol), water. The reaction temperature may vary depending on the kinds of the starting materials, etc. but is usually in the range of 50 to 90° C.

Process 4

The compound of the formula (Ic):

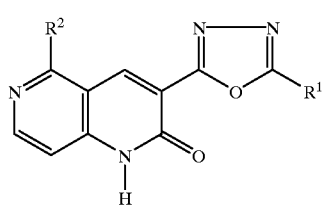

(Ic)

wherein $R^1$ and $R^2$ are the same as defined above, can be prepared by subjecting a compound of the formula (VI):

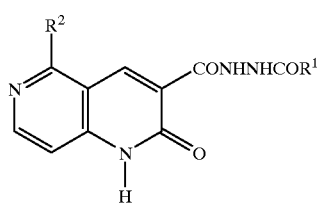

(VI)

wherein $R^1$ and $R^2$ are the same as defined above, to an intramolecular cyclization reaction.

The cyclization reaction may be carried out in the presence of a dehydrating agent, but may usually be carried out by heating the compound in an appropriate solvent which does not affect the reaction. The solvent includes aromatic hydrocarbons (e.g. benzene, toluene, xylene), ethers (e.g. tetrahydrofuran, dioxane), N,N-dimethylformamide. These solvents may be used alone or in combination of two or more thereof. The reaction temperature may vary depending on the kinds of the starting materials, etc. but is usually in the range of 50 to 150° C., preferably 80 to 120° C.

The cyclization reaction may also be carried out in a similar manner as described in EP-A2-0588500 in an appropriate solvent which does not affect the reaction in the presence of a trivalent phosphorus compound (e.g. triphenylphosphine) and a dialkylazodicarboxylic acid ester. The reaction temperature may vary depending on the kinds of the starting materials, etc. but is usually in the range of 0 to 110° C., preferably 0 to 60° C.

The compounds (I) of this invention prepared by the above processes 1 to 4 may be isolated and purified by a conventional procedures such as chromatography, recrystallization, or re-precipitation.

The compounds (I) of this invention may be obtained in the form of a free base or an acid addition salt thereof depending, for example, on the kinds of the selected starting materials to be used, on the reaction conditions and procedures. The acid addition salt may be converted into a free base by treating it by a conventional base such as an alkali metal carbonate and an alkali metal hydroxide. In addition, the free base may be converted into an acid addition salt by treating it with a kind of various acids in a usual manner.

The processes for preparing the starting compounds are explained below.

The compounds of the formulae (II) to (VI) used in the above Processes 1 to 4 are novel compounds and can be prepared by a process as shown in the following Reaction Scheme-1.

Reaction Scheme-1

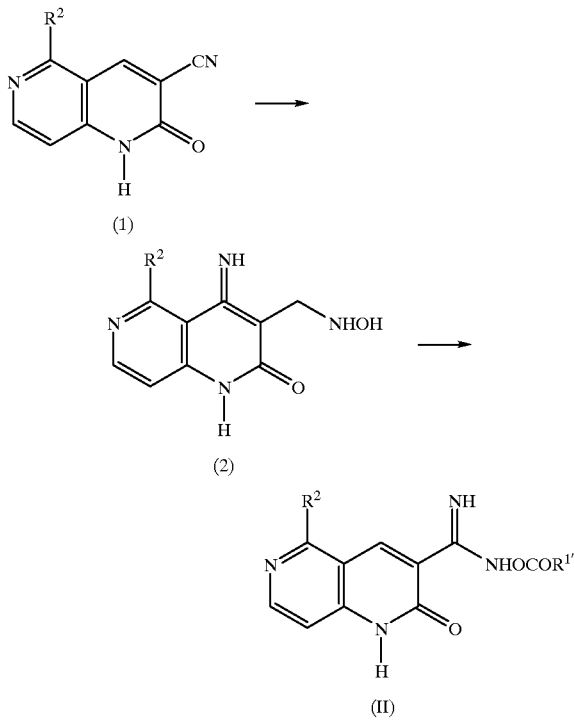

wherein $R^{1'}$ is the same as $R^1$ except a lower alkoxy group, and $R^2$ is the same as defined above.

The compound (1) is reacted with hydroxylamine in a usual manner to give the compound (2), and said compound is reacted with a reactive derivative at the carboxyl group of a carboxylic acid of the formula: $R^{1'}$ COOH (wherein $R^{1'}$ is as defined above) in the presence of a base to give the compound of the formula (II).

The compound of the formula (III) used in the above Process 1 may be prepared by a process as shown in the following Reaction Scheme-2.

Reaction Scheme-2

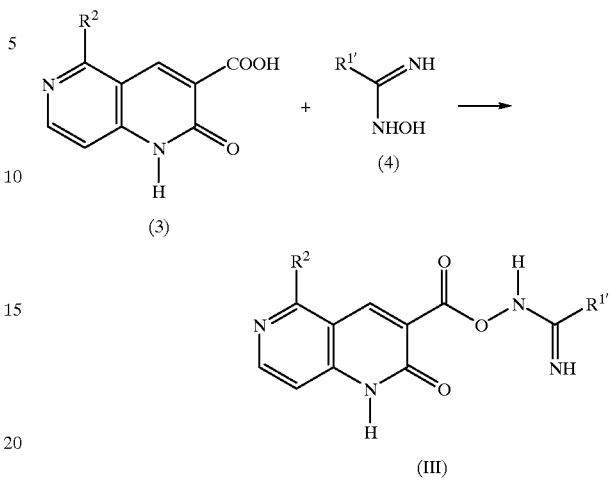

wherein $R^{1'}$ is the same as $R^1$ except a lower alkoxy group, and $R^2$ is the same as defined above.

The compound (3) or a reactive derivative at the carboxyl group thereof is reacted with a kind of various amidoximes (4) under a reaction condition for a conventional amidation to give the compound of the formula (III).

The compound of the formula (IV) used in the above Process 2 can be prepared by a process as shown in the following Reaction Scheme-3.

Reaction Scheme-3

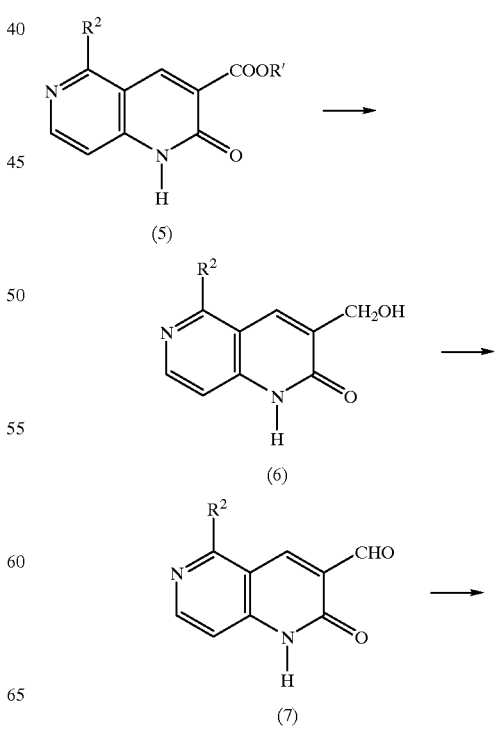

-continued

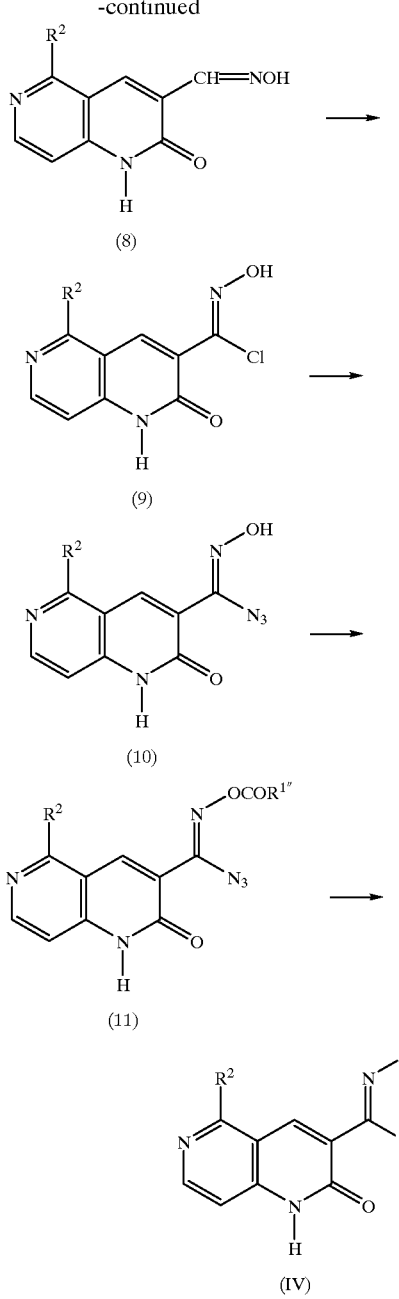

(8)

(9)

(10)

(11)

(IV)

wherein $R^{1''}$ is a lower alkoxy group, R' is a lower alkyl group or a substituted or unsubstituted benzyl group, Ph means a phenyl group and $R^2$ is the same as defined above.

The compound (5) is reduced with a reducing agent such as sodium borohydride, tetrabutylammonium borohydride, lithium aluminum hydride in an appropriate solvent to give the compound (6) and then said compound is oxidized with an activated manganese dioxide in an appropriate solvent to give the compound (7).

The compound (7) is reacted with hydroxylamine under a condition for the conventional oxime-forming reaction to give the compound (8), and then said compound is reacted with N-chlorosuccinimide in a similar manner as described, for example, in Journal of Organic Chemistry, vol. 45, p.3916 (1980) to give the compound (9).

The compound (9) is reacted with sodium azide in an appropriate solvent in a similar manner as described, for example, in Synthesis, p.102 (1979) to give the compound (10), and then, said compound is reacted with a compound of the formula: $XCOR^{1''}$ (wherein X is a halogen atom and $R^{1''}$ is a lower alkoxy group) in an appropriate solvent in a similar manner as described, for example, in Synthesis, p.843 (1986) to give the compound (11), and said compound is further reacted with triphenylphosphine to give the compound of the formula (IV).

The compound of the formula (V) used in the above Process 3 can be prepared by a process as shown in the following Reaction Scheme-4.

Reaction Scheme-4

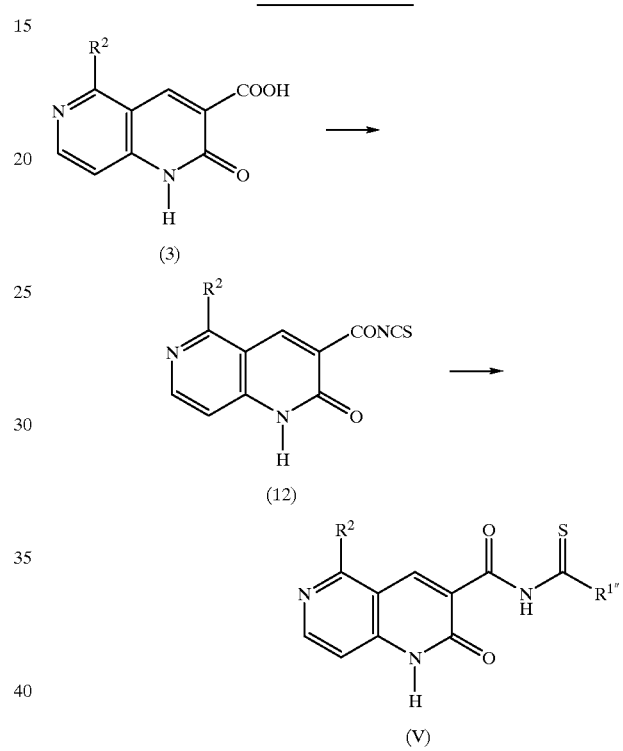

(3)

(12)

(V)

wherein $R^{1'}$ is a lower alkoxy group and $R^2$ is the same as defined above.

The compound (3) or a reactive derivative at the carboxyl group thereof is reacted with an alkali metal thiocyanate in an appropriate solvent to give the compound (12) and then said compound is subjected to alcoholysis to give the compound (V).

The compound of the formula (VI) used in the above Process 4 can be prepared by a process as shown in the following Reaction Scheme-5.

Reaction Scheme-5

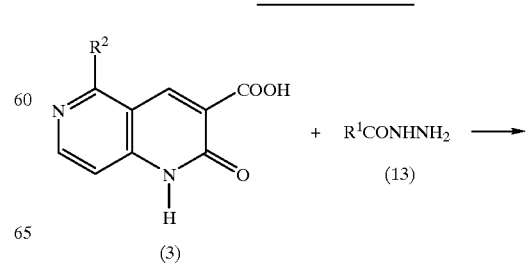

(3) + $R^1CONHNH_2$ (13) → wherein $R^1$ and $R^2$ are the same as defined above.

The compound (3) or a reactive derivative at the carboxyl group thereof is reacted with a hydrazide (13) of the formula: $R^1CONHNH_2$ (wherein $R^1$ is the same as defined above) by a conventional amidation reaction to give the compound of the formula (IV).

The compound (VI) may also be prepared by a two step reaction, that is, by reacting the compound (3) or a reactive derivative at the carboxyl group thereof with the hydrazine by a conventional amidation reaction, followed by reacting the resultant with a reactive derivative at the carboxyl group of a carboxylic acid of the formula: $R^1COOH$ ($R^1$ is the same as defined above).

A process for preparing the intermediate of the formula (I') is explained below.

The compounds of the formula (I') wherein R is a cyano group or a carboxyl group, that is, the compound (1) and the compound (3) as used in the Reaction Scheme-1 and Reaction Scheme-2, can be prepared in a similar manner as described, for example, in Journal of Heterocyclic Chemistry, vol. 27, p.2085 (1990) or Journal of Medicinal Chemistry, vol. 35, p.4858 (1992) as shown in the following Reaction Scheme-6.

wherein X is a di-lower alkylamino group, a cyclic amino group, a hydroxy group, a halogen atom, or a lower alkoxy group, R' is a lower alkyl group or a substituted or unsubstituted benzyl group, and $R^2$ is the same as defined above.

In the above reaction scheme, the compound (16) can be prepared by reacting the compound (14) with N,N-dimethylformamide dimethylacetal or an orthoformic acid ester in an appropriate solvent in a similar manner as described, for example, in Heterocycles, vol. 29, p.1517 (1989) or in Journal of Heterocyclic Chemistry, vol. 27, p.511 (1990) to give the compound (15), followed by reacting it with cyanoacetamide in the presence of an appropriate base.

The compound (16) thus prepared is further reacted with N,N-dimethylformamide dimethylacetal in an appropriate solvent to give the compound (17), and then said compound is reacted with ammonia or an ammonium salt in an appropriate solvent to give the compound (1). The compound (1) thus obtained is hydrolyzed with an acid or an alkali by a conventional method to give the compound (3).

In addition, the compounds of the formula (I') wherein R is a lower alkoxycarbonyl group or a substituted or unsubstituted benzyloxycarbonyl group, for example, the compounds (5) can be prepared by esterifying the compound (1) or the compound (3) by a conventional method.

Pharmacological Experiments

The pharmacological properties of the compounds (I) of the present invention are illustrated by the following experiments with representative compounds.

Experiment 1

Benzodiazepine Receptor Binding Assay

According to the method disclosed in Life Science Vol. 20, p. 2101 (1977), the benzodiazepine receptor binding assay was carried out.

A crude synaptosome membrane fraction prepared from brains of Wistar rats (age: 7 to 8 weeks) was suspended in 15 mM Tris-HCl buffer (pH 7.4) containing 118 mM sodium chloride, 4.8 mM potassium chloride, 1.28 mM calcium chloride and 1.2 mM magnesium sulfate in a concentration of 1 g (wet weight) of brain per 20 ml of buffer to give a receptor membrane source. [3H]-diazepam was used as a labelled ligand.

A test compound (a known amount), [3H]-diazepam (final concentration; 1.5 nM), receptor membrane and the above buffer were added to a test tube (final volume: 1 ml). The reaction was started by addition of the receptor membrane. The test tube was incubated at 0° C. for 20 minutes, and the reaction mixture was terminated by rapid filtration through Whatman GF/B glass fiber filter attached to a Cell-harvester (manufactured by Brandell). Immediately, the collected labelled ligand-bound receptor membrane was washed three times with ice-cold 50 mM Tris-HCl buffer (pH 7.7, each 5 ml). The radioactivity on the filter was measured by a liquid scintillation counter to determine the amount of the $[^3H]$-diazepam bound to the receptor membrane (total binding). Separately, the same procedures were repeated except 1 μM diazepam was added, and thereby the amount of $[^3H]$-diazepam bound to the receptor membrane (non-specific binding) was measured likewise. This non-specific binding was deducted from the total binding to give the specific binding. Based on the specific binding thus obtained, the inhibitory activity (IC50) of the test compound was determined by probit method.

The results are shown in the following Tables 1 to 4.

TABLE 1

BENZODIAZEPINE RECEPTOR BINDING Assay

| Ex. No. | BZP-receptor Binding $IC_{50}$ (nM) |
|---|---|
| 1 | 2.28 |
| 3 | 3.58 |
| 4 | 1.65 |
| 5 | 1.64 |
| 6 | 2.98 |
| 7 | 2.39 |
| 9 | 1.62 |
| 10 | 8.08 |
| 11 | 9.77 |
| 12 | 7.89 |
| 14 | 9.45 |
| 15 | 6.16 |
| 16 | 3.69 |
| 17 | 0.69 |
| 18 | 2.04 |
| 19 | 6.37 |
| 20 | 2.77 |
| 21 | 4.21 |
| 22 | 3.76 |
| 23 | 1.76 |
| 24 | 4.47 |
| 25 | 1.84 |
| 26 | 0.67 |
| 27 | 0.96 |
| 28 | 1.25 |
| 29 | 5.28 |
| 31 | 1.64 |
| 32 | 3.29 |
| 33 | 5.50 |
| 37 | 3.91 |
| 38 | 1.31 |
| 39 | 2.86 |
| 40 | 7.45 |
| 44 | 2.62 |
| 45 | 0.96 |

TABLE 1-continued

BENZODIAZEPINE RECEPTOR BINDING Assay

| Ex. No. | BZP-receptor Binding $IC_{50}$ (nM) |
|---|---|
| 46 | 2.15 |
| 47 | 2.33 |
| 48 | 1.49 |
| 49 | 1.11 |
| 50 | 0.88 |
| 51 | 0.79 |
| 52 | 0.74 |
| 54 | 1.21 |
| 55 | 1.66 |

TABLE 2

| Ex. No. | BZP-receptor Binding $IC_{50}$ (nM) |
|---|---|
| 56 | 2.71 |
| 57 | 1.55 |
| 58 | 1.52 |
| 59 | 1.98 |
| 60 | 2.01 |
| 61 | 1.04 |
| 86 | 2.21 |
| 87 | 2.35 |
| 88 | 4.63 |
| 89 | 10.5 |
| 91 | 0.61 |
| 92 | 0.75 |
| 93 | 1.75 |
| 94 | 4.49 |
| 95 | 1.09 |
| 96 | 2.82 |
| 97 | 4.64 |
| 98 | 8.56 |
| 99 | 1.67 |
| 100 | 1.31 |
| 102 | 0.81 |
| 103 | 0.83 |
| 104 | 5.18 |
| 105 | 1.08 |
| 106 | 1.96 |
| 107 | 6.56 |
| 108 | 2.14 |
| 109 | 1.75 |
| 110 | 1.16 |
| 111 | 2.06 |
| 112 | 2.68 |
| 113 | 2.18 |
| 114 | 1.08 |
| 115 | 1.52 |
| 116 | 1.17 |
| 117 | 1.41 |
| 118 | 1.28 |
| 119 | 2.53 |
| 120 | 1.59 |
| 121 | 0.78 |
| 122 | 0.87 |
| 123 | 1.12 |
| 173 | 0.94 |
| 175 | 1.21 |

TABLE 3

| Ex. No. | BZP-receptor Binding IC$_{50}$ (nM) |
| --- | --- |
| 176 | 2.13 |
| 176 | 2.33 |
| 178 | 2.31 |
| 179 | 4.73 |
| 180 | 1.22 |
| 183 | 1.55 |
| 186 | 1.55 |
| 187 | 6.42 |
| 188 | 1.20 |
| 189 | 0.84 |
| 190 | 1.57 |
| 192 | 4.22 |
| 193 | 4.10 |
| 194 | 1.06 |
| 195 | 4.01 |
| 196 | 4.60 |
| 197 | 1.97 |
| 198 | 1.03 |
| 199 | 1.55 |
| 200 | 0.92 |
| 201 | 1.84 |
| 202 | 2.09 |
| 203 | 1.97 |
| 204 | 5.51 |
| 205 | 4.77 |
| 206 | 1.16 |
| 207 | 3.42 |
| 208 | 4.14 |
| 209 | 1.28 |
| 210 | 3.41 |
| 211 | 0.82 |
| 212 | 1.26 |
| 213 | 2.07 |
| 215 | 2.47 |
| 216 | 1.17 |
| 217 | 1.34 |
| 218 | 2.58 |
| 219 | 2.03 |
| 220 | 0.93 |
| 221 | 0.72 |
| 222 | 1.49 |
| 224 | 3.57 |
| 225 | 2.12 |
| 226 | 1.41 |

TABLE 4

| Ex. No. | BZP-receptor Binding IC$_{50}$ (nM) |
| --- | --- |
| 227 | 1.46 |
| 228 | 1.59 |
| 229 | 1.12 |
| 230 | 0.9 |
| 231 | 0.71 |
| 232 | 6.48 |
| 233 | 1.58 |
| 234 | 0.84 |
| 235 | 0.91 |
| 236 | 1.61 |
| 237 | 1.86 |
| 238 | 1.38 |
| 240 | 2.51 |
| 241 | 6.08 |
| 242 | 1.87 |
| 243 | 1.81 |
| 244 | 4.12 |
| 245 | 0.81 |
| 246 | 1.46 |
| 247 | 1.39 |
| 311 | 1.91 |

Experiment-2

TBPS Binding Assay

Method

The TBPS (t-butylbicyclophosphonothionate) binding assay and the preparation of the membrane specimen were done in a similar manner to the method of Biggio, G. et al. [cf. European Journal of Pharmacology, vol. 161, pp.173–180 (1989)].

The membrane specimen was prepared from the cerebral cortex of Wistar rats (age: 7 to 8 weeks) by the following procedure. That is, to the cerebral cortex was added a 50-fold volume of an ice-cooled buffer (a 50 mM Tris-citrate buffer containing 100 mM sodium chloride, pH 7.4) and the mixture was homogenized at 0–4° C. and then centrifuged at 20,000 g for 20 minutes. The pellets thus obtained were once subjected to homogenization in a buffer and centrifugation by the same procedure as above and then kept in freezed state at −80° C. for more than 20 hours. On the test day, the freezed pellets were thawed and then subjected twice to the homogenization-centrifugation procedure as described above. The pellets thus obtained were suspended in a buffer in a concentration of 1 g (wet weight) per 25 ml of buffer to give a membrane specimen to be used in the binding assay.

The binding assay was carried out by the following procedure by using as a labelled ligand [$^{35}$S]TBPS (final concentration; 0.4 nM) and as a non-labelled ligand Picrotoxin (final concentration; 100 μM) in the presence of GABA (final concentration; 1 μM).

A test compound (a known amount), [$^{35}$S] labelled ligand, the membrane specimen, GABA and a buffer were added to a test tube (final volume; 1 ml). The reaction was started by addition of the membrane specimen (200 μl). The test tube was incubated at 25° C. for 90 minutes, and the reaction was terminated by filtration through Wattman GF/B glass fiber filter (which was previously dipped in 0.01% polyethylenimine for one day) attached to a Cell-harvester (manufactured by Brandell), and thereby, the labelled ligand-bound membrane was collected onto the filter. Immediately, the collected labelled ligand-bound membrane was washed with a ice-cooled 50 mM Tris-HCl buffer (pH 7.7, each 5 ml) three times. Subsequently, the filter was moved into a liquid scintillation vial and thereto was added a liquid scintillation cocktail (ACS-II, manufactured by Amersham, USA, 10 ml) and allowed to stand for a fixed period of time. Thereafter, the radioactivity on the filter was measured by a liquid scintillation counter (2000CA type, manufactured by Paccard, USA) to determine the total binding amount. Separately, the same procedures were repeated in the presence of Picrotoxin to determine the non-specific binding amount. The non-specific binding amount was deducted from the total binding amount to give the specific binding amount. The binding activity of the test compound was calculated by a variation rate, i.e., a rate of the specific binding amount of the test compound to the specific binding amount in control (using a solvent).

Evaluation Criteria

+% value means to exhibit inverse agonistic properties, −% value means to exhibit agonistic properties and 0% means to exhibit antagonistic properties.

The results are shown in Table 5 and Table 6.

TABLE 5

TBPS Binding Test

| Ex. No. | Variation Rate (%) |
|---|---|
| 2 | 53 |
| 3 | 12 |
| 4 | 20 |
| 5 | 21 |
| 6 | 15 |
| 7 | 12 |
| 8 | 13 |
| 11 | 21 |
| 13 | 24 |
| 14 | 38 |
| 16 | 38 |
| 17 | 25 |
| 18 | 10 |
| 20 | −13 |
| 21 | 21 |
| 23 | −23 |
| 24 | 22 |
| 36 | 15 |
| 38 | 25 |
| 43 | 28 |
| 45 | −9 |
| 47 | −11 |
| 48 | 18 |
| 50 | 40 |
| 52 | −11 |
| 55 | −16 |
| 58 | 15 |
| 86 | 12 |
| 87 | 32 |
| 88 | 41 |
| 89 | 22 |
| 91 | 38 |
| 92 | 32 |
| 93 | 34 |
| 94 | 34 |
| 95 | 13 |
| 96 | 16 |
| 100 | −23 |
| 102 | 33 |
| 103 | 21 |
| 105 | 25 |
| 106 | 20 |
| 107 | 17 |
| 123 | 12 |

TABLE 6

| Ex. No. | Variation Rate (%) |
|---|---|
| 173 | 18 |
| 175 | 28 |
| 176 | 39 |
| 177 | 29 |
| 178 | 25 |
| 179 | 37 |
| 180 | 13 |
| 181 | 13 |
| 182 | 19 |
| 183 | 8 |
| 184 | 17 |
| 185 | 19 |
| 186 | 21 |
| 187 | 27 |
| 188 | 34 |
| 189 | 29 |
| 190 | 34 |
| 191 | 18 |
| 192 | 13 |
| 193 | 44 |
| 194 | 32 |
| 196 | −9 |
| 198 | 11 |
| 200 | 17 |
| 202 | 22 |
| 203 | 17 |
| 206 | −13 |
| 210 | 15 |
| 211 | 24 |
| 212 | 27 |
| 213 | 26 |
| 224 | −12 |
| 228 | −10 |
| 229 | 10 |
| 233 | 31 |
| 240 | −13 |
| 241 | −14 |
| 244 | −15 |
| 245 | 13 |
| 247 | 16 |

Experiment 3

Test of Increasing Activity on Pentylen-tetrazol-induced Convulsion

It is known that benzodiazepine receptor inverse agonists increase convulsion induced by pentylentetrazol [cf. Progress in Neuro-Psychopharmacology and Biological Psychiatry, vol. 12, p.951 (1988)]. Some compounds of the present invention were tested as to the activities of increasing the pentylentetrazol-induced convulsion.

A test compound (compounds disclosed in working examples) was orally administered to ddY male mice (weight; 22–25 g, five mice/group) in an amount of 5–100 mg/kg. Fifteen minutes later, pentylentetrazol (70 mg/kg, which amount does not induce tonic convulsion by said compound alone) was injected subcutaneously into the mice, and immediately, the mice were observed as to the appearance of tonic convulsion at the hind leg for 30 minutes. The effects were evaluated by the number of mice among five mice, of which the convulsion increasing effects were observed. The results are shown in Table 7.

TABLE 7

| Ex. No. | Dose (mg/kg, po) | Effects (number of animals) |
|---|---|---|
| 4 | 10 | 4/5 |
| 5 | 5 | 5/5 |
| 6 | 100 | 4/5 |
| 11 | 10 | 4/5 |
| 18 | 20 | 3/5 |
| 86 | 10 | 2/5 |
| 88 | 10 | 5/5 |
| 89 | 50 | 5/5 |

TABLE 7-continued

| Ex. No. | Dose (mg/kg, po) | Effects (number of animals) |
|---|---|---|
| 94 | 50 | 4/5 |
| 102 | 10 | 5/5 |
| 103 | 10 | 2/5 |
| 105 | 50 | 4/5 |
| 173 | 20 | 5/5 |
| 183 | 20 | 4/5 |
| 184 | 50 | 5/5 |
| 186 | 50 | 4/5 |
| 191 | 10 | 5/5 |
| 192 | 100 | 5/5 |
| 200 | 50 | 4/5 |
| 210 | 10 | 4/5 |
| 213 | 10 | 5/5 |
| 220 | 20 | 4/5 |
| 247 | 50 | 4/5 |

As is shown in the above results, compounds embodying the present invention showed high selective affinity for benzodiazepine receptor and hence are useful as a drug for acting onto benzodiazepine receptor. Although some of the compounds of this invention have also agonistic properties, the compounds of this invention are particularly useful as an inverse agonist. The compounds having inverse agonistic properties are expected to be used in clinical fields entirely different from those of agonists, for example, as a psycho-analeptic drug or a drug for the treatment of dysmnesia in senile dementia or Alzheimer's disease.

PHARMACEUTICAL USE OF THE COMPOUNDS OF THIS INVENTION

The compounds of this invention may be administered either orally, parentally or intrarectally when used as a drug for acting onto benzodiazepine receptor, but preferably orally. The dosage of the compounds varies according to the route of the administration, conditions and ages of the patients, or the types of the treatment (e.g. prophylaxis or treatment) and the like, but it is usually in the range of 0.01 to 10 mg/kg/day, preferably in the range of 0.02 to 5 mg/kg/day.

The present compounds may be administered in the form of a conventional pharmaceutical preparation in admixture with a conventional pharmaceutically acceptable carrier or diluent. The pharmaceutically acceptable carrier or diluent may be any conventional one which is used in this field and does not react with the present compound, for example, lactose, glucose, mannitol, dextran, starch, white sugar, magnesium aluminate metasilicate, synthetic aluminum silicate, crystalline cellulose, sodium carboxymethylcellulose, calcium carboxy-methylcellulose, hydroxypropyl starch, ion-exchange resin, methyl cellulose, gelatin, gum arabic, hydroxypropyl cellulose, lower-substituted hydroxypropyl cellulose, hydroxypropyl-methyl cellulose, polyvinylpyrrolidone, polyvinyl alcohol, light silicic anhydride, magnesium stearate, talc, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, liquid paraffin, white petrolatum, nonionic surfactant, propylene glycol, water, and the like.

Pharmaceutical preparations are tablets, capsules, granules, powders, syrups, suspensions, suppositories, gels, injection preparations, and the like. These preparations may be prepared by a conventional method. When a liquid preparation is prepared, it may previously be in the form of a solid preparation which is dissolved or suspended in water or a solvent when used. In addition, tablets or granules may be coated by a conventional method, and injection preparations prepared by dissolving the compound (I) of the present invention or an acid addition salt thereof in distilled water for injection, or a physiological saline solution, but if necessary, it may be dissolved in a isotonic solution, and further, a pH adjustor, a buffer or a preservative may be added thereto.

These pharmaceutical preparations may contain the present compound in an amount of more than 0.01 % by weight, preferably 0.05 to 70 % by weight, and may contain other pharmacologically active ingredients.

BEST MODE FOR CARRYING OUT THE INVENTION

The compounds of this invention are illustrated by the following Examples. The symbols in tables means as follows. Me: methyl, Et: ethyl, n-Pr: n-propyl, i-Pr: isopropyl, c-Pr: cyclopropyl, n-Bu: n-butyl, t-Bu: tert-butyl, Ph: phenyl. The position of substituents is indicated like this,.for example, 3-Me-Ph means 3-methylphenyl.

EXAMPLE 1

Preparation of 3-(5-cyclopropyl-1,2,4-oxadiazol-3-yl)-5-methyl-1,6-naphthyridin-2(1H)-one:

(1) To a solution of hydroxylamine hydrochloride (4.17 g) in water (50 ml) was added sodium carbonate (3.18 g) with stirring under ice cooling. To the solution were subsequently added ethanol (200 ml) and 1,2-dihydro-5-methyl-2-oxo-1,6-naphthyridine-3-carbonitrile (3.70 g), and the mixture was refluxed for 2 hours. After distilling off the solvent under reduced pressure, water was added to the residue, and the precipitated crystals were separated by filtration. The product was washed with water, isopropanol, diisopropyl ether in this order, and dried to give 1,2-dihydro-5-methyl-2-oxo-1,6-naphthyridin-3-amidoxime (4.2 g). This compound was used in the next reaction without being purified.

(2) To a suspension of the above amidoxime (1.09 g), sodium carbonate (0.83 g) and methyl ethyl ketone (200 ml) was added cyclopropanecarbonyl chloride (0.57 g) with stirring under ice cooling, and the mixture was stirred at room temperature overnight. After distilling off the solvent under reduced pressure, water was added to the residue, and the precipitated crystals were separated by filtration, washed with water, isopropanol and diisopropyl ether in this order, and then dried. To the resulting crystals was added dimethylformamide (DMF) (50 ml) and the mixture was stirred at 130° C. for 5 hours. After distilling off the solvent under reduced pressure, isopropanol was added to the residue, and the crystals were separated by filtration. The resulting crystals were recrystallized from ethanol-chloroform to give the title compound (0.65 g) as colorless crystals. M.p. 259–260° C.

EXAMPLES 2 to 85

In the same manner as described in Example 1, the corresponding starting materials were reacted to give the compounds of Examples 2 to 85 as shown in Tables 8 to 12.

TABLE 8

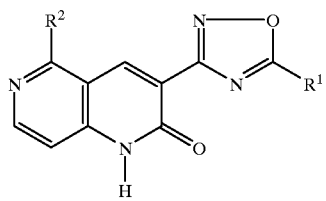

| Ex. No. | R¹ | R² | M.p. (° C.) | Solvent for recrystallization |
|---|---|---|---|---|
| 2 | Me | Me | >300 | CHCl₃—EtOH |
| 3 | Me | i-Bu | 231–233 | MeCN |
| 4 | Me | Ph | 302–303 | EtOH |
| 5 | Me | 3-F—Ph | >300 | EtOH |
| 6 | Me | 4-F—Ph | >300 | EtOH |
| 7 | Me | 3-Cl—Ph | >300 | CHCl₃—MeOH |
| 8 | Me | 4-Cl—Ph | >300 | CHCl₃—MeOH |
| 9 | Me | 3-Me—Ph | 285–287 | EtOH |
| 10 | Me | 4-Me—Ph | >300 | MeCN |
| 11 | Me | 4-MeO—Ph | 298–300 | CHCl₃—MeCN |
| 12 | Et | H | 249–251 | MeCN |
| 13 | Et | Me | 246–247 | CHCl₃—EtOH |
| 14 | Et | Et | 239–240 | EtOH |
| 15 | Et | n-Pr | 222–223 | MeCN |
| 16 | Et | i-Pr | 288–289 | MeCN |
| 17 | Et | c-Pr | 266–268 | MeCN |
| 18 | Et | 2-Me-c-Pr | 285–287 | EtOH |
| 19 | Et | n-Bu | 223–225 | MeCN |
| 20 | Et | i-Bu | 227–229 | MeCN |

TABLE 9

| Ex. No. | R¹ | R² | M.p. (° C.) | Solvent for recrystallization |
|---|---|---|---|---|
| 21 | Et | c-Bu | 271–272 | EtOH |
| 22 | Et | n-pentyl | 216–218 | MeCN |
| 23 | Et | c-hexyl | 295–296 | CHCl₃—MeCN |
| 24 | Et | c-hexyl-CH₂ | 235–237 | EtOH |
| 25 | Et | 3-c-hexenyl | 281–282 | EtOH |
| 26 | Et | Ph | 289–290 | EtOH |
| 27 | Et | 3-F-Ph | >300 | EtOH |
| 28 | Et | 4-F-Ph | >300 | EtOH |
| 29 | Et | 3-Cl-Ph | >300 | CHCl₃—MeOH |
| 30 | Et | 4-Cl-Ph | >300 | EtOH |
| 31 | Et | 3-Me-Ph | 290–291 | CHCl₃—EtOH |
| 32 | Et | 4-Me-Ph | >300 | EtOH |
| 33 | Et | 4-MeO-Ph | >300 | CHCl₃—EtOH |
| 34 | n-Pr | Me | 252–254 | EtOH |
| 35 | n-Pr | Et | 216–218 | MeCN |
| 36 | n-Pr | i-Pr | 273–274 | MeCN |
| 37 | n-Pr | c-Pr | 234–236 | MeCN |
| 38 | n-Pr | Ph | 284–285 | EtOH |
| 39 | n-Pr | 3-F-Ph | >300 | EtOH |
| 40 | n-Pr | 4-F-Ph | >300 | EtOH |
| 41 | i-Pr | Me | 266–267 | EtOH |

TABLE 10

| Ex. No. | R¹ | R² | M.p. (° C.) | Solvent for recrystallization |
|---|---|---|---|---|
| 42 | i-Pr | Et | 247–249 | MeCN |
| 43 | i-Pr | i-Pr | 265–267 | MeCN |
| 44 | i-Pr | c-Pr | 276–278 | EtOH |
| 45 | i-Pr | Ph | 280–281 | EtOH |
| 46 | i-Pr | 3-F-Ph | >300 | EtOH |
| 47 | i-Pr | 4-F-Ph | >300 | EtOH |
| 48 | c-Pr | Et | 233–236 | MeCN |
| 49 | c-Pr | n-Pr | 217–219 | MeCN |
| 50 | c-Pr | i-Pr | 268–269 | MeCN |
| 51 | c-Pr | c-Pr | 242–245 | MeCN |
| 52 | c-Pr | Ph | 281–282 | EtOH |
| 53 | c-Pr | 3-F-Ph | >300 | EtOH |
| 54 | c-Pr | 4-F-Ph | >300 | EtOH |
| 55 | c-Pr | 3-Cl-Ph | >300 | EtOH |
| 56 | c-Pr | 4-Cl-Ph | >300 | EtOH |
| 57 | c-Pr | 3-Me-Ph | 274–276 | EtOH |
| 58 | c-Pr | 4-Me-Ph | >300 | EtOH |
| 59 | c-Pr | 4-MeO-Ph | 297–299 | EtOH |
| 60 | i-propenyl | c-Pr | 265–268 | MeCN |
| 61 | vinyl | c-Pr | 250–252 | MeCN |

TABLE 11

| Ex. No. | R¹ | R² | M.p. (° C.) | Solvent for recrystallization |
|---|---|---|---|---|
| 62 | i-Pr | 2-Cl-Ph | | |
| 63 | i-Pr | 3-Cl-Ph | 283–285 | EtOH |
| 64 | i-Pr | 4-Cl-Ph | >300 | EtOH |
| 65 | i-Pr | 2-Br-Ph | | |
| 66 | i-Pr | 3-Br-Ph | >300 | CHCl₃—EtOH |
| 67 | i-Pr | 4-Br-Ph | >300 | CHCl₃—EtOH |
| 68 | i-Pr | 2-Me-Ph | >300 | MeCN |
| 69 | i-Pr | 3-Me-Ph | 281–283 | MeCN |
| 70 | i-Pr | 4-Me-Ph | 293–294 | EtOH |
| 71 | i-Pr | 3-MeO-Ph | 202–204 | MeCN |
| 72 | i-Pr | 3-CF₃-Ph | 258–261 | EtOH |
| 73 | i-Pr | n-Pr | 217–219 | MeCN |
| 74 | n-Bu | Ph | 264–266 | MeCN |
| 75 | i-BU | Ph | 281–283 | MeCN |
| 76 | t-Bu | Ph | 294–296 | MeCN |
| 77 | c-hexyl | Ph | 276–277 | MeCN |
| 78 | CH₂OCH₃ | Ph | | |
| 79 | Ph | Ph | >300 | DMF |
| 80 | 2-Cl-Ph | Ph | >300 | CHCl₃—EtOH |
| 81 | 3-Cl-Ph | Ph | >300 | DMF |
| 82 | 4-Cl-Ph | Ph | >300 | DMF |

TABLE 12

| Ex. No. | R¹ | R² | M.p. (° C.) | Solvent for recrystallization |
|---|---|---|---|---|
| 83 | 4-Me-Ph | Ph | >300 | DMF |
| 84 | 3-pyridyl | Ph | >300 | CHCl₃—EtOH |
| 85 | 2-furyl | Ph | >300 | EtOH |

EXAMPLE 86

Preparation of 3-(5-methyl-1,2,4-oxadiazol-3-yl)-5-(3-methoxyphenyl)-1,6-naphthyridin-2(1H)-one:

To a solution of acetic acid (0.90 g) in DMF (100 ml) was added N,N'-carbonyldiimidazole (2.43 g) and the mixture was stirred at 70° C. for 3 hours. To the solution was added 1,2-dihydro-5-(3-methoxyphenyl)-2-oxo-1,6-naphthyridin-3-amidoxime (3.10 g) prepared in the same manner as described in Example 1(1), and the mixture was stirred at 70° C. for 2 hours and further at 130° C. for 1 hour. The reaction mixture was concentrated to dryness under reduced pressure, and water was added to the residue, and the precipitated crystals were separated by filtration and washed with water, isopropanol and diisopropyl ether in this order and then dried. The resulting crystals were subjected to silica gel column chromatography and eluted with chloroform-methanol (50:1). The resulting crystals were recrystallized from chloroform-ethanol to give the title compound (2.22 g) as colorless crystals. M.p. 286–288° C. Hydrochloride of the title compound, M.p. 281–282° C. (recrystallized from ethanol).

EXAMPLES 87 to 172

In the same manner as described in Example 86, the corresponding starting materials were reacted to give the compounds of Examples 87 to 172 as shown in Tables 13 to 17.

TABLE 13

| Ex. No. | $R^1$ | $R^2$ | M.p. (° C.) | Solvent for recrystallization |
|---|---|---|---|---|
| 87 | Me | 2-F—Ph | 287–288 | EtOH-i-Pr$_2$O |
| 88 | Me | 2-Cl—Ph | 262–264 | CHCl$_3$—MeOH |
| 89 | Me | 2-Me—Ph | 244–245 | MeCN |
| 90 | Me | 2-MeO—Ph | 260–262 | MeCN |
| 91 | Me | 2-furyl | 291–294 | MeOH |
| 92 | Me | 2-thienyl | >300 | CHCl$_3$—MeOH |
| 93 | Me | 3-thienyl | 292–294 | MeCN |
| 94 | Me | 4-pyridyl | >300 | EtOH-i-Pr$_2$O |
| 95 | Et | 2-F—Ph | 235–236 | EtOH-i-Pr$_2$O |
| 96 | Et | 2-Cl—Ph | 167–168 | EtOH |
| 97 | Et | 2-Me—Ph | 221–222 | EtOH |
| 98 | Et | 2-MeO—Ph | 229–230 | EtOH—I—Pr$_2$O |
| 99 | Et | 3-MeO—Ph | 246–247 | EtOH |
| 100 | Et | 1-naphthyl | 248–250 | MeCN |

TABLE 14

| Ex. No. | $R^1$ | $R^2$ | M.p. (° C.) | Solvent for recrystallization |
|---|---|---|---|---|
| 101 | Et | 2-naphthyl | 231–233 | MeCN |
| 102 | Et | 2-furyl | 278–280 | CHCl$_3$—MeCN |
| 103 | Et | 2-thienyl | 291–294 | CHCl$_3$—MeCN |
| 104 | Et | 5-Cl-2-thienyl | 280–281 | CHCl$_3$—EtOH |
| 105 | Et | 3-thienyl | >300 | EtOH |
| 106 | Et | 3-pyridyl | 292–293 | EtOH |
| 107 | Et | 4-pyridyl | >300 | CHCl$_3$—MeOH |
| 108 | n-Pr | 2-F-Ph | 242–243 | MeCN |
| 109 | n-Pr | 2-furyl | 264–266 | EtOH |
| 110 | n-Pr | 2-thienyl | 269–271 | EtOH |
| 111 | n-Pr | 3-thienyl | 296–297 | EtOH |
| 112 | i-Pr | 2-F-Ph | 265–267 | MeCN |
| 113 | i-Pr | 2-furyl | 274–276 | EtOH |
| 114 | i-Pr | 2-thienyl | 273–275 | MeCN |
| 115 | i-Pr | 3-thienyl | 297–299 | EtOH |
| 116 | c-Pr | 2-F-Ph | 133–135 | MeCN |
| 117 | c-Pr | 2-Cl-Ph | 270–272 | MeCN |
| 118 | c-Pr | 2-Me-Ph | 265–267 | MeCN |
| 119 | c-Pr | 2-MeO-Ph | 175–177 | MeCN |
| 120 | c-Pr | 3-MeO-Ph | 146–148 | EtOH |

TABLE 14-continued

| Ex. No. | $R^1$ | $R^2$ | M.p. (° C.) | Solvent for recrystallization |
|---|---|---|---|---|
| 121 | c-Pr | 2-furyl | 280–282 | CHCl$_3$—EtOH |
| 122 | c-Pr | 2-thienyl | >300 | CHCl$_3$—EtOH |
| 123 | c-Pr | 3-thienyl | 289–290 | EtOH |

TABLE 15

| Ex. No. | $R^1$ | $R^2$ | M.p. (° C.) | Solvent for recrystallization |
|---|---|---|---|---|
| 124 | n-Pr | 2-Cl-Ph | 213–215 | MeCN |
| 125 | n-Pr | 3-Cl-Ph | 298–300 | EtOH |
| 126 | n-Pr | 4-Cl-Ph | >300 | EtOH |
| 127 | Me | 2-Br-Ph | 270–273 | MeCN |
| 128 | Et | 2-Br-Ph | 149–151 | MeCN |
| 129 | c-Pr | 2-Br-Ph | 260–262 | MeCN |
| 130 | n-Pr | 2-Br-Ph | 293–296 | MeCN |
| 131 | Me | 3-Br-Ph | >300 | CHCl$_3$—EtOH |
| 132 | Et | 3-Br-Ph | >300 | EtOH |
| 133 | c-Pr | 3-Br-Ph | >300 | CHCl$_3$—EtOH |
| 134 | n-Pr | 3-Br-Ph | >300 | CHCl$_3$—EtOH |
| 135 | Me | 4-Br-Ph | >300 | CHCl$_3$—EtOH |
| 136 | Et | 4-Br-Ph | >300 | EtOH |
| 137 | c-Pr | 4-Br-Ph | >300 | CHCl$_3$—EtOH |
| 138 | n-Pr | 4-Br-Ph | >300 | CHCl$_3$—EtOH |
| 139 | n-Pr | 2-Me-Ph | 208–210 | MeCN |
| 140 | n-Pr | 3-Me-Ph | 226–228 | MeCN |
| 141 | n-Pr | 4-Me-Ph | 253–255 | MeCN |
| 142 | Me | 2-OH-Ph | | |
| 143 | Et | 2-OH-Ph | | |
| 144 | Me | 3-OH-Ph | | |
| 145 | Et | 3-OH-Ph | | |
| 146 | Me | 4-OH-Ph | | |

TABLE 16

| Ex. No. | $R^1$ | $R^2$ | M.p. (° C.) | Solvent for recrystallization |
|---|---|---|---|---|
| 147 | Et | 4-OH-Ph | | |
| 148 | n-Pr | 2-MeO-Ph | 193–194 | MeCN |
| 149 | n-Pr | 3-MeO-Ph | 239–241 | MeCN |
| 150 | Me | 3-CF$_3$-Ph | >300 | CHCl$_3$—EtOH |
| 151 | Et | 3-CF$_3$-Ph | >300 | EtOH |
| 152 | c-Pr | 3-CF$_3$-Ph | >300 | EtOH |
| 153 | n-Pr | 3-CF$_3$-Ph | 286–288 | EtOH |
| 154 | Me | 4-CF$_3$-Ph | >300 | CHCl$_3$—EtOH |
| 155 | Et | 4-CF$_3$-Ph | >300 | EtOH |
| 156 | c-Pr | 4-CF$_3$-Ph | >300 | CHCl$_3$—EtOH |
| 157 | Me | 3-CF$_3$O-Ph | >300 | EtOH |
| 158 | Et | 3-CF$_3$O-Ph | 271–273 | MeCN |
| 159 | c-Pr | 3-CF$_3$O-Ph | 237–239 | MeCN |
| 160 | Me | 4-CF$_3$O-Ph | | |
| 161 | Et | 4-CF$_3$O-Ph | >300 | EtOH |
| 162 | c-Pr | 4-CF$_3$O-Ph | >300 | EtOH |
| 163 | Me | n-Pr | 269–271 | MeCN |
| 164 | Me | i-Pr | 292–294 | MeCN |
| 165 | Me | c-Pr | >300 | MeCN |
| 166 | Me | n-Bu | 232–233 | MeCN |

TABLE 17

| Ex. No. | R¹ | R² | M.p. (° C.) | Solvent for recrystallization |
|---|---|---|---|---|
| 167 | n-Pr | n-Bu | 220–222 | MeCN |
| 168 | Me | c-hexyl | 283–286 | MeCN |
| 169 | CF₃ | Ph | | |
| 170 | CH₂OH | Ph | | |
| 171 | 2-thienyl | Ph | >300 | CHCl₃—EtOH |
| 172 | 3-furyl | Ph | >300 | EtOH |

EXAMPLE 173

Preparation of 3-(3-ethyl-1,2,4-oxadiazol-5-yl)-5-(2-thienyl)-1,6-naphthyridin-2(1H)-one:

To a solution of 1,2-dihydro-5-(2-thienyl)-2-oxo-1,6-naphthyridin-3-carboxylic acid (3.81 g) in DMF (50 ml) was added N,N'-carbonyldiimidazole (3.41 g) and the mixture was stirred at 700° C. for 4 hours. To the solution was added propionic amidoxime (1.85 g), and the mixture was stirred at 70° C. for 1 hour and further at 130° C. for 2 hours. The reaction mixture was concentrated to dryness under reduced pressure, and water was added to the residue, and the precipitated crystals were separated by filtration and washed with water, isopropanol and diisopropyl ether in this order and then dried. The resulting crystals were subjected to silica gel column chromatography and eluted with chloroform-methanol (50:1). The resulting crystals were recrystallized from chloroform-ethanol to give the title compound (2.60 g) as colorless crystals. M.p. 265–268° C.

EXAMPLES 174 to 307

In the same manner as described in Example 173, the corresponding starting materials were reacted to give the compounds of Examples 174 to 307 as shown in Tables 18 to 24.

TABLE 18

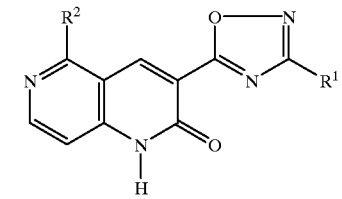

| Ex. No. | R¹ | R² | M.p. (° C.) | Solvent for recrystallization |
|---|---|---|---|---|
| 174 | Me | Me | >300 | EtOH |
| 175 | Me | Ph | >300 | EtOH |
| 176 | Me | 2-F—Ph | >300 | EtOH |
| 177 | Me | 3-F—Ph | >300 | EtOH |
| 178 | Me | 4-F—Ph | >300 | EtOH |
| 179 | Me | 2-Cl—Ph | 263–265 | MeCN |
| 180 | Me | 3-Cl—Ph | >300 | CHCl₃—EtOH |
| 181 | Me | 4-Cl—Ph | >300 | CHCl₃—EtOH |
| 182 | Me | 2-Me—Ph | 266–267 | MeCN |
| 183 | Me | 3-Me—Ph | 286–287 | EtOH |
| 184 | Me | 4-Me—Ph | >300 | EtOH |
| 185 | Me | 2-MeO—Ph | >300 | MeCN |
| 186 | Me | 3-MeO—Ph | 276–278 | EtOH |
| 187 | Me | 4-MeO—Ph | 287–289 | EtOH |
| 188 | Me | 2-furyl | >300 | EtOH |
| 189 | Me | 2-thienyl | >300 | EtOH |

TABLE 18-continued

| Ex. No. | R¹ | R² | M.p. (° C.) | Solvent for recrystallization |
|---|---|---|---|---|
| 190 | Me | 3-thienyl | 294–295 | MeCN |
| 191 | Et | Me | 259–260 | EtOH |

TABLE 19

| Ex. No. | R¹ | R² | M.p. (° C.) | Solvent for recrystallization |
|---|---|---|---|---|
| 192 | Et | n-Pr | 202–204 | MeCN |
| 193 | Et | i-Pr | 222–224 | MeCN |
| 194 | Et | c-Pr | 255–257 | MeCN |
| 195 | Et | n-Bu | 196–198 | MeCN |
| 196 | Et | i-Bu | 198–200 | MeCN |
| 197 | Et | c-hexyl | 254–257 | MeCN |
| 198 | Et | Ph | 276–277 | EtOH |
| 199 | Et | 2-F-Ph | 242–243 | EtOH-i-Pr₂O |
| 200 | Et | 3-F-Ph | >300 | EtOH |
| 201 | Et | 4-F-Ph | >300 | EtOH |
| 202 | Et | 2-Cl-Ph | 260–261 | MeCN |
| 203 | Et | 3-Cl-Ph | >300 | CHCl₃—MeOH |
| 204 | Et | 4-Cl-Ph | >300 | CHCl₃—EtOH |
| 205 | Et | 2-Me-Ph | 245–246 | MeCN |
| 206 | Et | 3-Me-Ph | 270–272 | MeCN |
| 207 | Et | 4-Me-Ph | 267–269 | EtOH |
| 208 | Et | 2-MeO-Ph | 225–226 | MeCN |
| 209 | Et | 3-MeO-Ph | 250–252 | MeCN |
| 210 | Et | 4-MeO-Ph | 266–268 | EtOH |
| 211 | Et | 2-furyl | 254–256 | EtOH |
| 212 | Et | 3-thienyl | 286–288 | EtOH |

TABLE 20

| Ex. No. | R¹ | R² | M.p. (° C.) | Solvent for recrystallization |
|---|---|---|---|---|
| 213 | Et | 4-pyridyl | >300 | MeCN |
| 214 | n-Pr | Me | 217–218 | EtOH |
| 215 | n-Pr | c-Pr | 201–202 | MeCN |
| 216 | n-Pr | Ph | 224–225 | EtOH |
| 217 | n-Pr | 2-F-Ph | 220–221 | EtOH |
| 218 | n-Pr | 3-F-Ph | 259–261 | EtOH |
| 219 | n-Pr | 4-F-Ph | 261–263 | EtOH |
| 220 | n-Pr | 2-furyl | 221–223 | EtOH |
| 221 | n-Pr | 2-thienyl | 225–227 | EtOH |
| 222 | n-Pr | 3-thienyl | 244–246 | EtOH |
| 223 | i-Pr | Me | 244–245 | EtOH |
| 224 | i-Pr | c-Pr | 275–277 | MeCN |
| 225 | i-Pr | Ph | 273–275 | MeCN |
| 226 | i-Pr | 2-F-Ph | 257–259 | MeCN |
| 227 | i-Pr | 3-F-Ph | 297–299 | EtOH |
| 228 | i-Pr | 4-F-Ph | 284–286 | EtOH |
| 229 | i-Pr | 2-furyl | 258–260 | EtOH |
| 230 | i-Pr | 2-thienyl | 260–262 | EtOH |
| 231 | i-Pr | 3-thienyl | 263–264 | EtOH |
| 232 | c-Pr | Me | 251–253 | MeCN |

TABLE 21

| Ex. No. | R¹ | R² | M.p. (° C.) | Solvent for recrystallization |
|---|---|---|---|---|
| 233 | c-Pr | i-Pr | 224–227 | MeCN |
| 234 | c-Pr | c-Pr | 241–243 | MeCN |
| 235 | c-Pr | Ph | 278–280 | EtOH |
| 236 | c-Pr | 2-F-Ph | 219–221 | MeCN |
| 237 | c-Pr | 3-F-Ph | 289–291 | EtOH |
| 238 | c-Pr | 4-F-Ph | 298–300 | EtOH |
| 239 | c-Pr | 2-Cl-Ph | 262–263 | MeCN |
| 240 | c-Pr | 3-Cl-Ph | >300 | EtOH |
| 241 | c-Pr | 4-Cl-Ph | >300 | EtOH |
| 242 | c-Pr | 2-Me-Ph | 239–240 | MeCN |
| 243 | c-Pr | 3-Me-Ph | 246–248 | EtOH |
| 244 | c-Pr | 4-Me-Ph | >300 | EtOH |
| 245 | c-Pr | 2-furyl | 277–278 | EtOH |
| 246 | c-Pr | 2-thienyl | 281–282 | EtOH |
| 247 | c-Pr | 3-thienyl | 280–281 | EtOH |
| 248 | n-Pr | 3-Cl-Ph | 293–295 | MeCN |
| 249 | i-Pr | 3-Cl-Ph | >300 | EtOH |
| 250 | n-Pr | 4-Cl-Ph | 287–289 | MeCN |
| 251 | i-Pr | 4-Cl-Ph | >300 | EtOH |
| 252 | Me | 2-Dr-Ph | 275–278 | MeCN |
| 253 | Et | 2-Br-Ph | 254–255 | MeCN |

TABLE 22

| Ex. No. | R¹ | R² | M.p. (° C.) | Solvent for recrystallization |
|---|---|---|---|---|
| 254 | c-Pr | 2-Br-Ph | 259–261 | MeCN |
| 255 | n-Pr | 2-Br-Ph | 226–229 | MeCN |
| 256 | i-Pr | 2-Br-Ph | 238–239 | MeCN |
| 257 | Me | 3-Br-Ph | >300 | CHCl₃—EtOH |
| 258 | Et | 3-Br-Ph | >300 | EtOH |
| 259 | c-Pr | 3-Br-Ph | >300 | EtOH |
| 260 | n-Pr | 3-Br-Ph | >300 | EtOH |
| 261 | i-Pr | 3-Br-Ph | >300 | EtOH |
| 262 | Me | 4-Br-Ph | >300 | CHCl₃—EtOH |
| 263 | Et | 4-Br-Ph | >300 | MeCN |
| 264 | c-Pr | 4-Br-Ph | >300 | EtOH |
| 265 | n-Pr | 4-Br-Ph | >300 | EtOH |
| 266 | i-Pr | 4-Br-Ph | >300 | EtOH |
| 267 | n-Pr | 2-Me-Ph | 228–230 | MeCN |
| 268 | i-Pr | 2-Me-Ph | 223–226 | MeCN |
| 269 | n-Pr | 3-Me-Ph | 220–221 | MeCN |
| 270 | i-Pr | 3-Me-Ph | 247–249 | MeCN |
| 271 | n-Pr | 4-Me-Ph | 252–253 | MeCN |
| 272 | i-Pr | 4-Me-Ph | >300 | MeCN |
| 273 | Me | 2-OH-Ph | | |

TABLE 23

| Ex. No. | R¹ | R² | M.p. (° C.) | Solvent for recrystallization |
|---|---|---|---|---|
| 274 | Et | 2-OH-Ph | | |
| 275 | Me | 3-OH-Ph | | |
| 276 | Et | 3-OH-Ph | | |
| 277 | Me | 4-OH-Ph | | |
| 278 | Et | 4-OH-Ph | | |
| 279 | n-Pr | 2-MeO-Ph | 220–222 | MeCN |
| 280 | i-Pr | 2-MeO-Ph | 267–269 | MeCN |
| 281 | n-Pr | 3-MeO-Ph | 219–220 | MeCN |
| 282 | i-Pr | 3-MeO-Ph | 225–226 | MeCN |
| 283 | n-Pr | 4-MeO-Ph | 220–222 | MeCN |
| 284 | i-Pr | 4-MeO-Ph | 272–274 | MeCN |
| 285 | Me | 3-CF₃-Ph | >300 | EtOH |
| 286 | Et | 3-CF₃-Ph | >300 | EtOH |
| 287 | c-Pr | 3-CF₃-Ph | 288–290 | EtOH |
| 288 | Me | 4-CF₃-Ph | >300 | EtOH |
| 289 | Me | 3-CF₃O-Ph | >300 | EtOH |
| 290 | Et | 3-CF₃O-Ph | 293–295 | MeCN |
| 291 | c-Pr | 3-CF₃O-Ph | 252–254 | MeCN |
| 292 | Et | 4-CF₃O-Ph | 279–281 | EtOH |
| 293 | c-Pr | 4-CF₃O-Ph | 279–281 | MeCN |

TABLE 24

| Ex. No. | R¹ | R² | M.p. (° C.) | Solvent for recrystallization |
|---|---|---|---|---|
| 294 | Me | n-Pr | 242–244 | MeCN |
| 295 | c-Pr | n-Pr | 204–205 | MeCN |
| 296 | Me | c-Pr | >300 | EtOH |
| 297 | Ph | Ph | >300 | CHCl₃—EtOH |
| 298 | 2-Cl-Ph | Ph | >300 | CHCl₃—EtOH |
| 299 | 3-Cl-Ph | Ph | 263–265 | DMF |
| 300 | 4-Cl-Ph | Ph | >300 | DMF |
| 301 | 2-Me-Ph | Ph | >300 | EtOH |
| 302 | 3-Me-Ph | Ph | 266–267 | CHCl₃—EtOH |
| 303 | 4-Me-Ph | Ph | 286–287 | CHCl₃—EtOH |
| 304 | 2-pyridyl | Ph | >300 | EtOH |
| 305 | 3-pyridyl | Ph | >300 | EtOH |
| 306 | 4-pyridyl | Ph | >300 | EtOH |
| 307 | 2-thienyl | Ph | >300 | EtOH |

EXAMPLE 308

Preparation of 3-(5-ethyl-1,3,4-oxadiazol-2-yl)-5-(2-thieyl)1,6-naphthyridin-2(1H)-one:

(1) A solution of 1,2-dihydro-5-(2-thienyl)-2-oxo-1,6-naphthyridine-3-carboxylic acid (1.36 g) and N,N'-carbonyldimidazole (1.22 g) in DMF (50ml) was stirred at 70° C. for 4 hours. To the solution was added propionylhydrazide (0.53 g), and the mixture was stirred at 70° C. for 2 hours. The reaction mixture was concentrated to dryness under reduced pressure, and isopropanol was added to the residue, and the precipitated crystals were separated by filtration. The product was washed with isopropanol and diisopropyl ether in this order, and dried to give 1,2-dihydro-N'-propionyl-5-(2-thienyl)-2-oxo-1,6-naphthyridin-3-carbohydrazide (1.21 g) as yellow crystals. This compound was used in the next reaction without being purified.

(2) To a suspension of the above carbohydrazide (1.09 g), triphenylphosphine (1.57 g) and triethylamine (1.06 g) in tetrahydrofuran (THF) (50 ml) was added dropwise diethyl azodicarboxylate (1.04 g) under ice cooling. The mixture was stirred at 70° C. for 4 hours. After cooling, water was added to the mixture, and then the mixture was concentrated under reduced pressure, and isopropanol was added to the residue. The precipitated crystals were separated by filtration and dried. The resulting crystals were subjected to silica gel column chromatography and eluted with chloroform-methanol (50:1). The crystals were recrystallized from ethanol to give the title compound (0.21 g) as colorless crystals. M.p. >300° C.

EXAMPLES 309 to 368

In the same manner as described in Example 308, the corresponding starting materials were reacted to give the compounds of Examples 309 to 368 as shown in Tables 25 to 27.

TABLE 25

[Structure: R² on pyridine-naphthyridine-one core with oxadiazole bearing R¹]

| Ex. No. | R¹ | R² | M.p. (° C.) | Solvent for recrystallization |
|---|---|---|---|---|
| 309 | Me | Me | >300 | MeCN |
| 310 | Et | Me | 258–259 | EtOH |
| 311 | Et | Ph | 258–259 | MeCN |
| 312 | n-Pr | Me | 209–210 | MeCN |
| 313 | i-Pr | Me | 250–251 | EtOH |
| 314 | c-Pr | Me | >300 | EtOH |
| 315 | Me | 3-F—Ph | >300 | CHCl₃—EtOH |
| 316 | Et | 3-F—Ph | >300 | EtOH |
| 317 | c-Pr | 3-F—Ph | 288–290 | EtOH |
| 318 | n-Pr | 3-F—Ph | 277–279 | EtOH |
| 319 | i-Pr | 3-F—Ph | 241–243 | MeCN |
| 320 | Me | 3-Br—Ph | 246–248 | EtOH |
| 321 | Et | 3-Br—Ph | 292–293 | CHCl₃—EtOH |
| 322 | c-Pr | 3-Br—Ph | >300 | MeCN |
| 323 | Et | 4-Br—Ph | >300 | EtOH |
| 324 | c-Pr | 4-Br—Ph | >300 | CHCl₃—EtOH |
| 325 | c-Pr | 2-Me—Ph | 283–285 | MeCN |
| 326 | Me | 3-Me—Ph | >300 | EtOH |
| 327 | Et | 3-Me—Ph | 258–260 | MeCN |

TABLE 26

| Ex. No. | R¹ | R² | M.p. (° C.) | Solvent for recrystallization |
|---|---|---|---|---|
| 328 | c-Pr | 3-Me-Ph | 244–246 | MeCN |
| 329 | n-Pr | 3-Me-Ph | 233–235 | MeCN |
| 330 | i-Pr | 3-Me-Ph | 187–189 | MeCN |
| 331 | Me | 4-Me-Ph | >300 | CHCl₃—EtOH |
| 332 | Et | 4-Me-Ph | >300 | EtOH |
| 333 | c-Pr | 4-Me-Ph | >300 | EtOH |
| 334 | n-Pr | 4-Me-Ph | >300 | EtOH |
| 335 | i-Pr | 4-Me-Ph | >300 | EtOH |
| 336 | Me | 2-OH-Ph | | |
| 337 | Et | 2-OH-Ph | | |
| 338 | Me | 3-OH-Ph | | |
| 339 | Et | 3-OH-Ph | | |
| 340 | Me | 4-OH-Ph | | |
| 341 | Et | 4-OH-Ph | | |
| 342 | Et | 2-MeO-Ph | 267–269 | MeCN |
| 343 | Me | 3-MeO-Ph | >300 | EtOH |
| 344 | Et | 3-MeO-Ph | 272–273 | MeCN |
| 345 | c-Pr | 3-MeO-Ph | 294–296 | MeCN |
| 346 | n-Pr | 3-MeO-Ph | 199–201 | MeCN |
| 347 | i-Pr | 3-MeO-Ph | 228–230 | MeCN |
| 348 | Me | 2-thienyl | >300 | CHCl₃—EtOH |
| 349 | c-Pr | 2-thienyl | >300 | EtOH |
| 350 | n-Pr | 2-thienyl | 292–294 | EtOH |

TABLE 27

| Ex. No. | R¹ | R² | M.p. (° C.) | Solvent for recrystallization |
|---|---|---|---|---|
| 351 | i-Pr | 2-thienyl | 293–296 | EtOH |
| 352 | Me | Ph | >300 | EtOH |
| 353 | c-Pr | Ph | >300 | MeCN |
| 354 | n-Pr | Ph | >300 | MeCN |
| 355 | n-BU | Ph | 281–283 | MeCN |
| 356 | c-hexyll | Ph | 251–253 | MeCN |
| 357 | Ph | Ph | >300 | DMF |
| 358 | 2-Cl-Ph | Ph | >300 | CHCl₃—EtOH |
| 359 | 3-Cl-Ph | Ph | >300 | DMF |
| 360 | 4-Cl-Ph | Ph | >300 | DMF |
| 361 | 2-Me-Ph | Ph | >300 | EtOH |
| 362 | 3-Me-Ph | Ph | >300 | CHCl₃—EtOH |
| 363 | 4-Me-Ph | Ph | >300 | CHCl₃—EtOH |
| 364 | 2-pyridyl | Ph | >300 | CHCl₃—EtOH |
| 365 | 3-pyridyl | Ph | >300 | CHCl₃—EtOH |
| 366 | 4-pyridyl | Ph | >300 | CHCl₃—EtOH |
| 367 | 2-thienyl | Ph | >300 | CHCl₃—EtOH |
| 368 | 2-furyl | Ph | >300 | EtOH |

EXAMPLE 369

Preparation of 1,2-dihydro-5-methyl-2-oxo-1,6-naphthyridine-3-carbonitrile:

(1) A mixture of acetylacetone (41 ml), N,N-dimethylformamide dimethylacetal (106.2 ml) and THF (200 ml) was stirred at room temperature for 3 hours. After distilling off the solvent under reduced pressure, the residue was added dropwise to a solution prepared by dissolving metal sodium (13.8 g) in ethanol (600 ml) and adding thereto cyanoacetamide (33.6 g), and the mixture was refluxed for one hour. The reaction mixture was ice-cooled, and the precipitated crystals were separated by filtration. The crystals were dissolved in water (1 liter) and then weakly acidified with 3N hydrochloric acid. The precipitated crystals were separated by filtration and recrystallized from DMF-methanol to give 5-acetyl-6-methyl-1,2-dihydro-2-oxo-3-pyridinecarbonitrile (60 g) as colorless crystals. M.p. 230° C.

(2) A solution of the above carbonitrile (30 g), N.N-dimethylformamide dimethylacetal (25 ml) and DMF (150 ml) was stirred at room temperature overnight. The precipitated crystals were separated by filtration, washed with methanol and then dried. The crystals thus obtained and ammonium acetate (21.9 g) were added to DMF (300 ml), and the mixture was stirred at 130° C. for 3 hours. The reaction mixture was concentrated under reduced pressure, and water was added to the residue, and the resulting crystals were separated by filtration and recrystallized from DMF to give the title compound (Compound No. 1)(25 g) as colorless crystals. M.p. 278° C.

In the same manner as described in Example 369, the corresponding starting materials were reacted to give the compounds of Compound Nos. 2 to 43 as shown in Tables 28 to 29.

TABLE 28

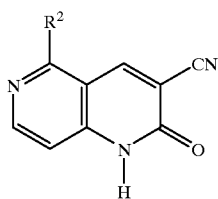

| Comp. No. | R² | M.p. (° C.) |
|---|---|---|
| 2 | H | >290 |
| 3 | Et | 268 |
| 4 | n-Pr | 259 |
| 5 | i-Pr | 283 |
| 6 | c-Pr | 276 |
| 7 | 2-Me-c-Pr | 242 |
| 8 | n-Bu | 259 |
| 9 | i-Bu | 236 |
| 10 | c-Bu | 270 |
| 11 | n-pentyl | 265 |
| 12 | c-hexyl | >290 |
| 13 | c-hexyl-CH₂ | 269 |
| 14 | 3-c-hexenyl | >290 |
| 15 | Ph | >290 |
| 16 | 2-F—Ph | >290 |
| 17 | 3-F—Ph | >290 |
| 18 | 4-F—Ph | >290 |
| 19 | 2-Cl—Ph | >290 |
| 20 | 3-Cl—Ph | >290 |
| 21 | 4-Cl—Ph | >290 |

TABLE 29

| Comp. No. | R² | M.p. (° C.) |
|---|---|---|
| 22 | 2-Br-Ph | 291–294 |
| 23 | 3-Br-Ph | 280–282 |
| 24 | 4-Br-Ph | |
| 25 | 2-Me-Ph | >290 |
| 26 | 3-Me-Ph | >290 |
| 27 | 4-Me-Ph | >290 |
| 28 | 2-CF₃-Ph | |
| 29 | 3-CF₃-Ph | 291–294 |
| 30 | 4-CF₃-Ph | >300 |
| 31 | 2-MeO-Ph | 289 |
| 32 | 3-MeO-Ph | >290 |
| 33 | 4-MeO-Ph | 278 |
| 34 | 3-CF₃O-Ph | 264–266 |
| 35 | 4-CF₃O-Ph | >300 |
| 36 | 1-naphthyl | >290 |
| 37 | 2-naphthyl | >290 |
| 38 | 2-furyl | >290 |
| 39 | 2-thienyl | >290 |
| 40 | 5-Cl-2-thienyl | >290 |
| 41 | 3-thienyl | >290 |
| 42 | 3-pyridyl | >290 |
| 43 | 4-pyridyl | 285 |

EXAMPLE 370

Preparation of 1,2-dihydro-5-(2-thienyl)-2-oxo-1,6-naphthyridine-3-carboxylic acid:

A mixture of 1,2-dihydro-5-(2-thienyl)-2-oxo-1,6-naphthyridine-3-carbonitrile (10.0 g), ethanol (300 ml) and 10N NaOH (300 ml) was refluxed overnight. After cooling, the reaction mixture was neutralized with acetic acid, and the precipitated crystals were separated by filtration, washed with water, isopropanol and diisopropyl ether in this order and then dried to give the title compound (Compound No. 44)(10.5 g) as pale yellow crystals. M.p. 2780° C.

In the same manner as described in Example 370, the corresponding starting materials were reacted to give the compounds of Compound Nos. 45 to 86 as shown in Tables 30 to 31.

TABLE 30

| Comp. No. | R² | M.p. (° C.) |
|---|---|---|
| 45 | H | 246 |
| 46 | Me | 273 |
| 47 | Et | 268 |
| 48 | n-Pr | >290 |
| 49 | i-Pr | >290 |
| 50 | c-Pr | >290 |
| 51 | 2-Me-c-Pr | 286 |
| 52 | n-Bu | 248 |
| 53 | i-Bu | 259 |
| 54 | c-Bu | >290 |
| 55 | n-pentyl | 263 |
| 56 | c-hexyl | >290 |
| 57 | c-hexyl-CH₂ | >290 |
| 58 | 3-c-hexenyl | >290 |
| 59 | Ph | >290 |
| 60 | 2-F—Ph | >290 |
| 61 | 3-F—Ph | >290 |
| 62 | 4-F—Ph | >290 |
| 63 | 2-Cl—Ph | >290 |
| 64 | 3-Cl—Ph | >290 |

TABLE 31

| Comp. No. | R² | M.p. (° C.) |
|---|---|---|
| 65 | 4-Cl-Ph | >290 |
| 66 | 2-Br-Ph | 288–291 |
| 67 | 3-Br-Ph | >300 |
| 68 | 4-Br-Ph | >300 |
| 69 | 2-Me-Ph | >290 |
| 70 | 3-Me-Ph | >290 |
| 71 | 4-Me-Ph | >290 |
| 72 | 2-CF₃-Ph | |
| 73 | 3-CF₃-Ph | 275–278 |
| 74 | 4-CF₃-Ph | >300 |
| 75 | 2-MeO-Ph | 286 |
| 76 | 3-MeO-Ph | >290 |
| 77 | 4-MeO-Ph | >290 |
| 78 | 3-CF₃O-Ph | 265–268 |
| 79 | 4-CF₃O-Ph | >300 |
| 80 | 1-naphthyl | >290 |
| 81 | 2-naphthyl | >290 |
| 82 | 2-furyl | >290 |
| 83 | 5-Cl-2-thienyl | >290 |
| 84 | 3-thienyl | >290 |
| 85 | 3-pyridyl | >290 |
| 86 | 4-pyridyl | >290 |

Preparation 1

Capsules

| | |
|---|---|
| 3-(5-Methyl-1,2,4-oxadiazol-3-yl)-5-(3-methoxyphenyl)-1,6-naphthyridin-2(1H)-one | 5 g |
| Corn starch | 57 g |
| Lactose | 10 g |

|  |  |
|---|---|
| Crystalline cellulose | 25 g |
| Hydroxypropyl cellulose | 2 g |
| Light silicic anhydride | 0.5 g |
| Magnesium stearate | 0.5 g |

According to a conventional method, the above components are mixed and kneaded to give the granules, which are packed into 1000 capsules to give a capsule preparation (each 100 mg).

Preparation 2

Tablets

|  |  |
|---|---|
| 3-(5-Methyl-1,2,4-oxadiazol-3-yl)-5-(3-methoxyphenyl)-1,6-naphthyridin-2(1H)-one | 5 g |
| Corn starch | 20 g |
| Lactose | 30 g |
| Hydroxypropyl cellulose | 5 g |
| Low-substituted hydroxypropyl cellulose | 10 g |

According to a conventional method, the above components are mixed and kneaded, and thereto are added light silicic anhydride and magnesium stearate, and the mixture is tabletted to give tablets containing 5 mg of the active ingredient in each tablet.

Preparation 3

Powder

|  |  |
|---|---|
| 3-(5-Methyl-1,2,4-oxadiazol-3-yl)-5-(3-methoxyphenyl)-1,6-naphthyridin-2(1H)-one | 5 g |
| Corn starch | 173 g |
| Lactose | 300 g |
| Hydroxypropyl cellulose | 20 g |

According to a conventional method, the above components are mixed and kneaded, pulverized, and thereto is added light silicic anhydride (q.s.) to give 50-trituration.

INDUSTRIAL APPLICATION

The compounds of this invention have high selective affinity to benzodiazepine receptor and are useful as a drug for acting onto benzodiazepine receptor. Although some of the compounds of this invention have agonistic properties, the compounds of this invention are particularly useful as an inverse agonist. The compounds having inverse agonistic properties are expected to be used in clinical fields entirely different from those of agonists, for example, as psychoanaleptic drug or a drug for the treatment of dysmnesia in senile dementia or Alzheimer's disease.

What is claimed is:

1. A I 6-naphthyridin-2(1H)-one derivative of the formula (I'):

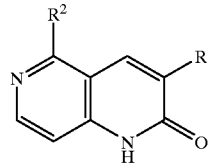

(I')

wherein R is a cyano group, a carboxyl group, a lower alkoxycarbonyl group, or a substituted or unsubstituted benzyloxycarbonyl groups and $R^2$ is a cyclo-lower alkyl group, a lower alkenyl group, a cyclo-lower alkenyl group, a lower alkynyl group, a substituted or unsubstituted aryl group or a substituted or unsubstituted heteroaromatic group, provided that $R^2$ is not a pyridyl group.

* * * * *

(12) REEXAMINATION CERTIFICATE (4715th)
United States Patent
Ohno et al.

(10) Number: US 6,277,993 C1
(45) Certificate Issued: Jan. 7, 2003

(54) INTERMEDIATES FOR 5-SUBSTITUTED-3-OXADIAZOLYL-1,6-NAPHTHYRIDIN-2(1H)-ONE DERIVATIVES

(75) Inventors: Kazunori Ohno, Ikoma (JP); Osamu Odai, Hirakata (JP); Kaoru Masumoto, Neyagawa (JP); Kiyoshi Furukawa, Shiga-ken (JP); Makoto Oka, Ibaraki (JP)

(73) Assignee: Dainippon Pharmaceutical Co., Ltd., Osaka (JP)

Reexamination Request:
No. 90/006,168, Dec. 28, 2001

Reexamination Certificate for:
Patent No.: 6,277,993
Issued: Aug. 21, 2001
Appl. No.: 09/654,782
Filed: Sep. 1, 2000

(*) Notice: This patent is subject to a terminal disclaimer.

Related U.S. Application Data

(62) Division of application No. 09/462,412, filed as application No. PCT/JP98/03134 on Jul. 19, 1998, now Pat. No. 6,172,079.

(30) Foreign Application Priority Data

Jul. 15, 1997 (JP) ............................................. 9-207179

(51) Int. Cl.$^7$ ............................................. C07D 471/04
(52) U.S. Cl. ....................................... 546/122; 546/123

(56) References Cited

U.S. PATENT DOCUMENTS 4,567,186 A  1/1986 Lesher et al.
4,650,806 A  3/1987 Lesher et al.

FOREIGN PATENT DOCUMENTS

EP   516392 A2   12/1992

*Primary Examiner*—Evelyn Huang

(57) ABSTRACT

A 5-substitute-3-oxadiazolyl-1,6-naphthyridin-2(1H)-one derivative of the formula (I):

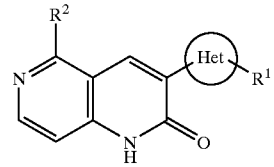

(I)

wherein Het is oxadiazolyl, $R^1$ is H, lower alkyl, cyclo-lower alkyl, trifluoromethyl, lower alkenyl, lower alkynyl, lower alkoxy, lower alkoxy-lower alkyl, hydroxy-lower alkyl, substituted or unsubstituted aryl, or substituted or unsubstituted heteroaromatic group, and $R^2$ is H, lower alkyl, cyclo-lower alkyl, cyclo-lower alkylmethyl, lower alkenyl, cyclo-lower alkenyl, lower alkynyl, substituted or unsubstituted aryl, or substituted or unsubstituted heteroaromatic group, or a pharmaceutically acceptable acid addition salt thereof, which has high selective affinity to benzodiazepine receptor and is useful particularly as a benzodiazepine inverse agonist, for example, as psychoanaleptic drug or a drug for the treatment of dysmnesia in senile dementia or Alzheimer's disease.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

1. A [1] *1,*6-naphthyridin-2(1H)-one derivative of the formula (I'):

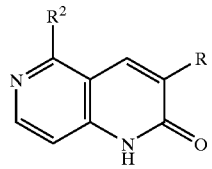

wherein R is a cyano group, a carboxyl group, a lower alkoxycarbonyl group, or a substituted or unsubstituted benzyloxycarbonyl [groups] *group,* and
$R^2$ is a [cyclo-lower alkyl group, a] lower alkenyl group, a cyclo-lower alkenyl group, a lower alkynyl group[,] *or* a substituted [or unsubstituted] aryl group [or a substituted or unsubstituted heteroaromatic group, provided that $R^2$ is not a pyridyl group].

* * * * *